US 6,471,670 B1

(12) United States Patent
Enrenfels et al.

(10) Patent No.: US 6,471,670 B1
(45) Date of Patent: Oct. 29, 2002

(54) FIBRIN SEALANT APPLICATOR SYSTEM

(76) Inventors: Karl Enrenfels, 583 Danbury Rd., Ridgefield, CT (US) 06877; Clifford L. Emmons, 17 Morin St., Oakville, CT (US) 06779; Chad Cimini, 1 Brewery Sq., Apt. S329, New Haven, CT (US) 06513; Csaba L. Reth, 303 Pansy Rd., Farfield, CT (US) 06430; Tim Van Leeuwen, 36 Flax Hill Rd., Brookfield, CT (US) 06804

( * ) Notice: Subject to any disclaimer, the term of this patent is extended or adjusted under 35 U.S.C. 154(b) by 0 days.

(21) Appl. No.: 09/411,090

(22) Filed: Oct. 4, 1999

Related U.S. Application Data
(60) Provisional application No. 60/103,073, filed on Oct. 5, 1998.

(51) Int. Cl.[7] .................. A61M 37/00; A61M 5/00; A61M 5/315
(52) U.S. Cl. .................. 604/88; 604/191; 604/218
(58) Field of Search .................. 604/82, 86–88, 604/92, 181, 184, 187, 191, 199, 200, 201, 218; 222/135, 137, 145.1, 145.4–145.6, 325–327; 239/398

(56) References Cited

U.S. PATENT DOCUMENTS

| 2,112,160 A | 3/1938 | Johnson |
| 3,223,083 A | 12/1965 | Cobey |
| 3,236,418 A | 2/1966 | Dalle et al. |
| 3,467,096 A | 9/1969 | Horn |
| 3,552,394 A | 1/1971 | Horn |
| 3,767,085 A | 10/1973 | Cannon et al. ............... 222/82 |
| 4,040,420 A | 8/1977 | Speer |
| 4,121,739 A | 10/1978 | Devaney et al. |
| 4,359,049 A | 11/1982 | Redl et al. |
| 4,631,055 A | 12/1986 | Redl et al. |
| 4,735,616 A | 4/1988 | Eibl et al. |
| 4,826,048 A | 5/1989 | Skorka et al. |
| 4,874,368 A | 10/1989 | Miller et al. |
| 4,902,281 A | 2/1990 | Avoy |
| 4,978,336 A | 12/1990 | Capozzi et al. |
| 4,979,942 A | 12/1990 | Wolf et al. |
| 5,116,315 A | 5/1992 | Capozzi et al. |
| 5,226,877 A | 7/1993 | Epstein |
| 5,464,396 A | 11/1995 | Barta et al. |
| 5,474,540 A | 12/1995 | Miller et al. |
| 5,505,704 A | 4/1996 | Pawelka et al. ............. 604/191 |
| 5,582,596 A | 12/1996 | Fukunaga et al. |
| 5,643,206 A | 7/1997 | Fischer |
| 5,665,067 A | 9/1997 | Linder et al. |
| 5,740,965 A | 4/1998 | Miyagi et al. ............... 239/423 |

FOREIGN PATENT DOCUMENTS

| EP | 0 835 667 | 4/1998 |
| WO | WO 98/02098 | 1/1998 |
| WO | WO 98/10703 | 3/1998 |
| WO | WO 98/10704 | 3/1998 |
| WO | WO 01/49361 A1 * | 1/2001 |

OTHER PUBLICATIONS

PCT International Search Report PCT/US99/23135.

* cited by examiner

Primary Examiner—Michael J. Hayes

(57) ABSTRACT

Fibrin sealant applicator systems are provided for dispensing a first and a second protein solution to form a biological adhesive which overcome the disadvantages of the prior art. The fibril sealant applicator system according to the present disclosure includes two piston-type sub-assemblies coupled to two vials storing a fibrinogen and a thrombin via a coupling unit. The piston-type sub-assemblies store sterilized water within reservoirs which are in fluid communication with the vials via the coupling unit. The water is forced into the vials to form a fibrinogen and a thrombin solution. The solutions are then drawn into the reservoirs and a Y-coupler is attached to the distal end of the piston-type sub-assemblies. The Y-coupler provides fluid communication between the reservoirs and a nozzle body for dispensing the solutions when distal pressure is created within the reservoirs to force the solutions towards the nozzle body.

31 Claims, 33 Drawing Sheets

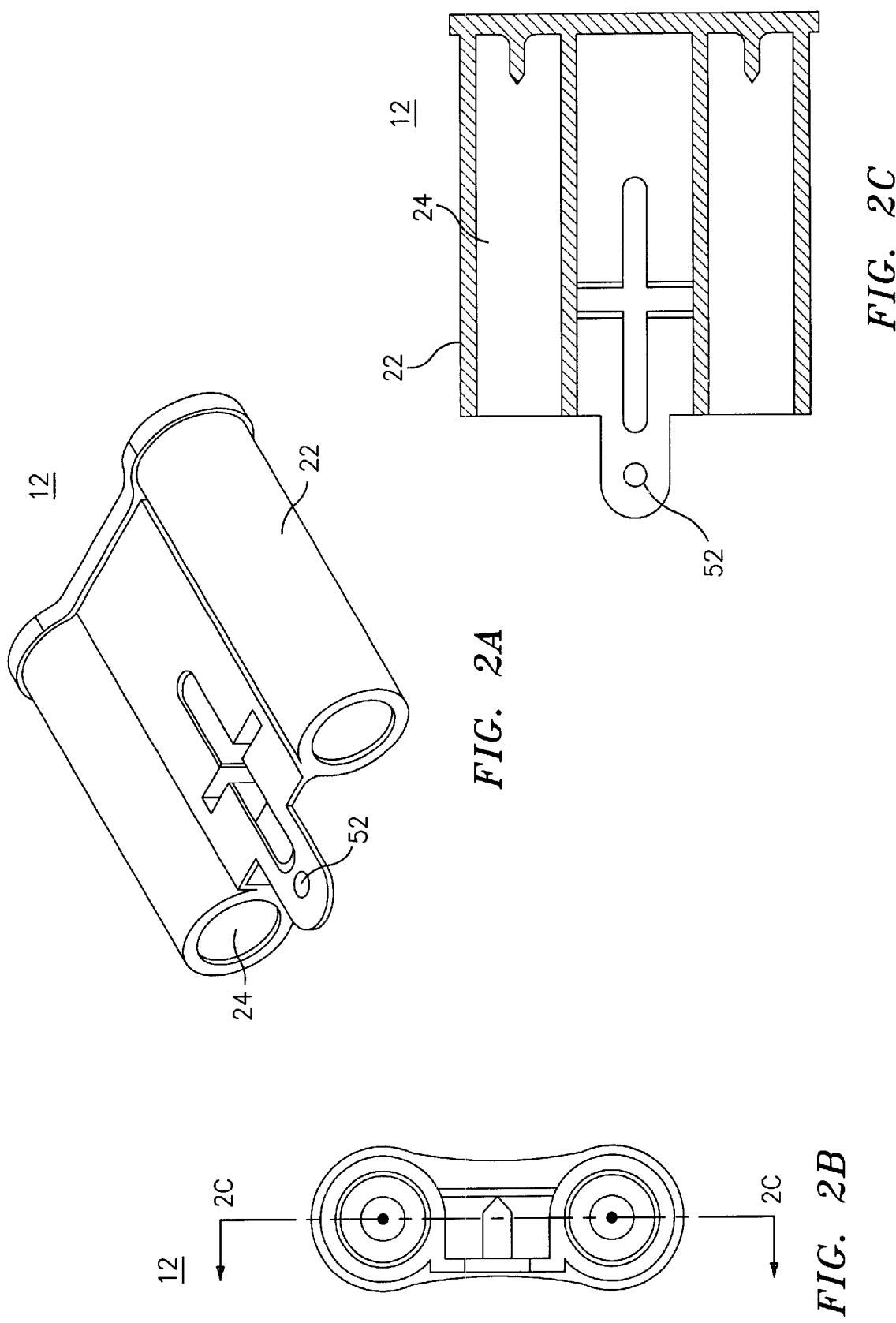

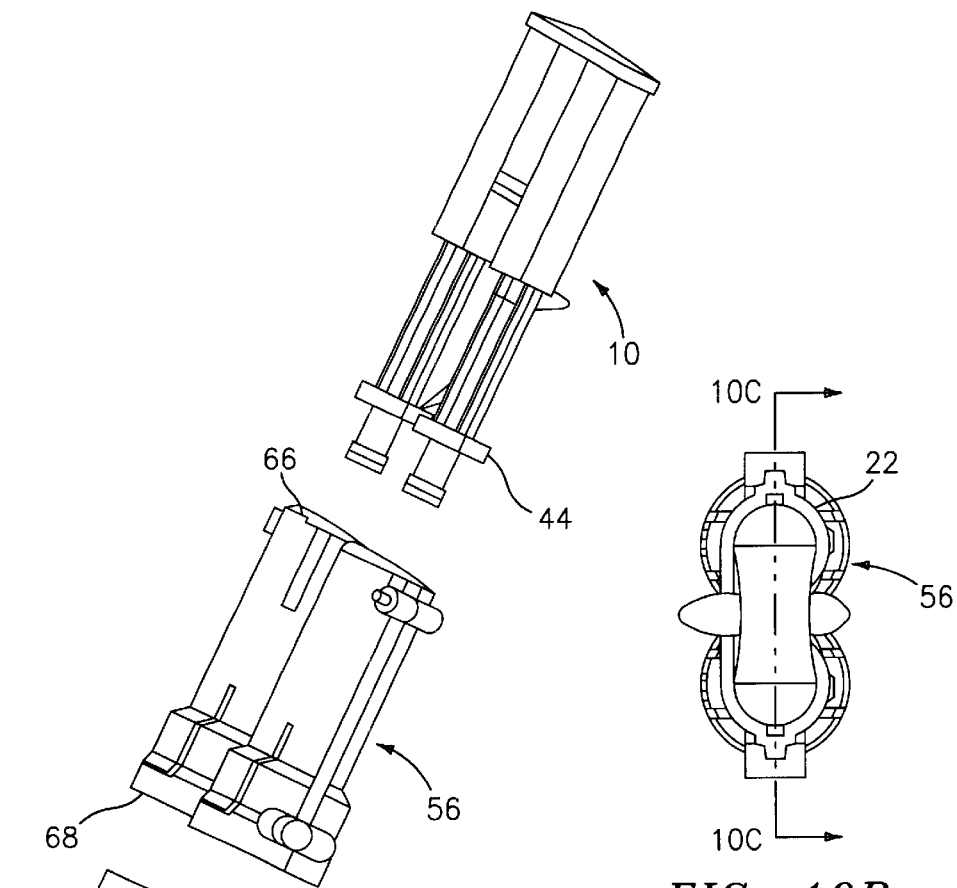
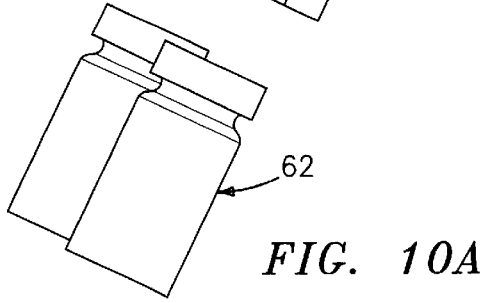
FIG. 10B
FIG. 10A
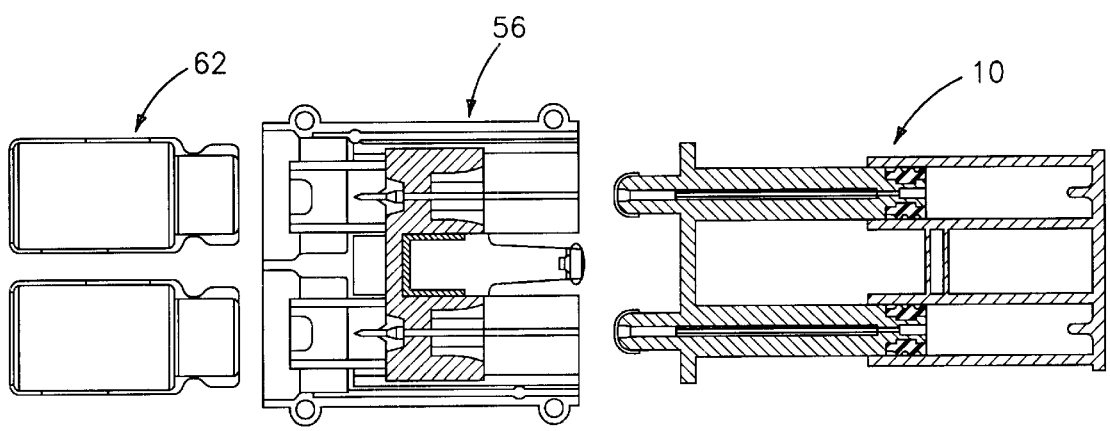
FIG. 10C

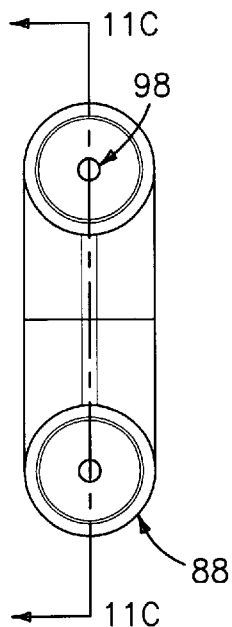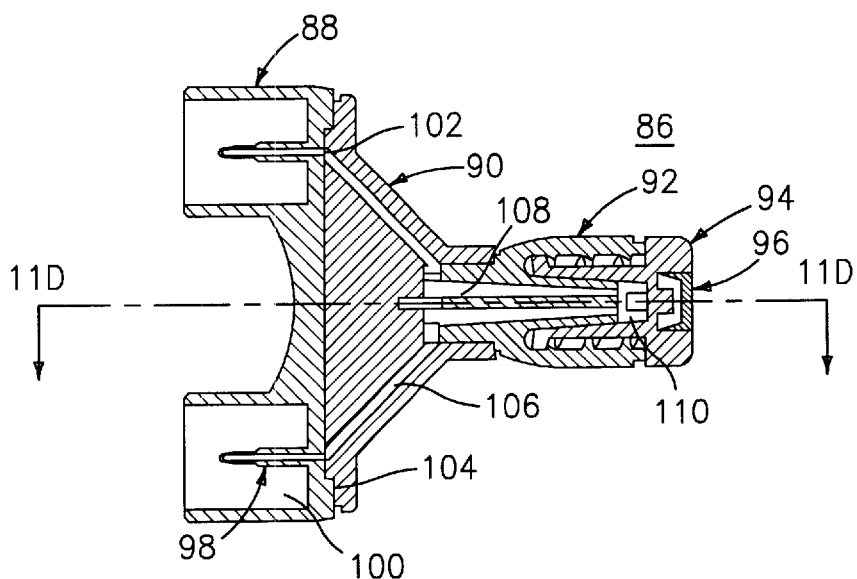
*FIG. 11B*  *FIG. 11C*
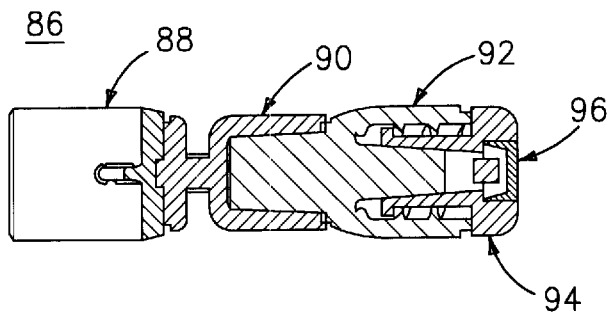
*FIG. 11D*

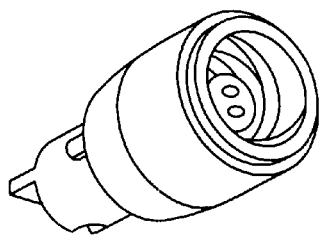
FIG. 14A
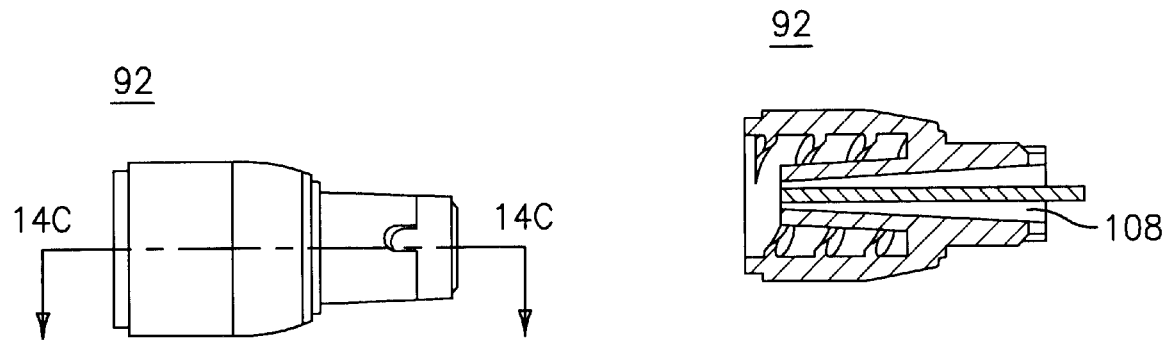
FIG. 14B
FIG. 14C
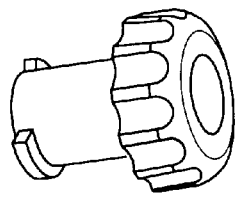
FIG. 15A
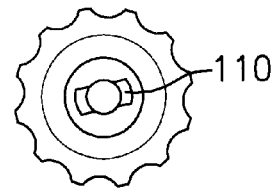
FIG. 15B

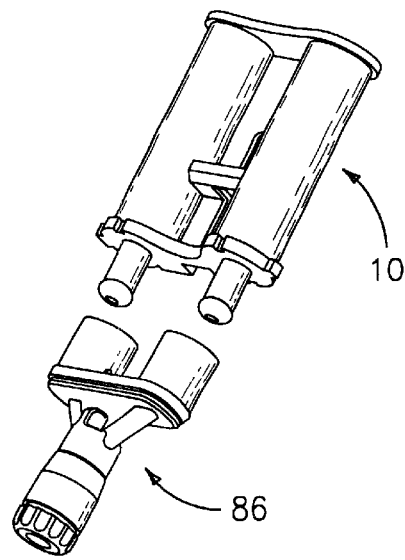
FIG. 16A
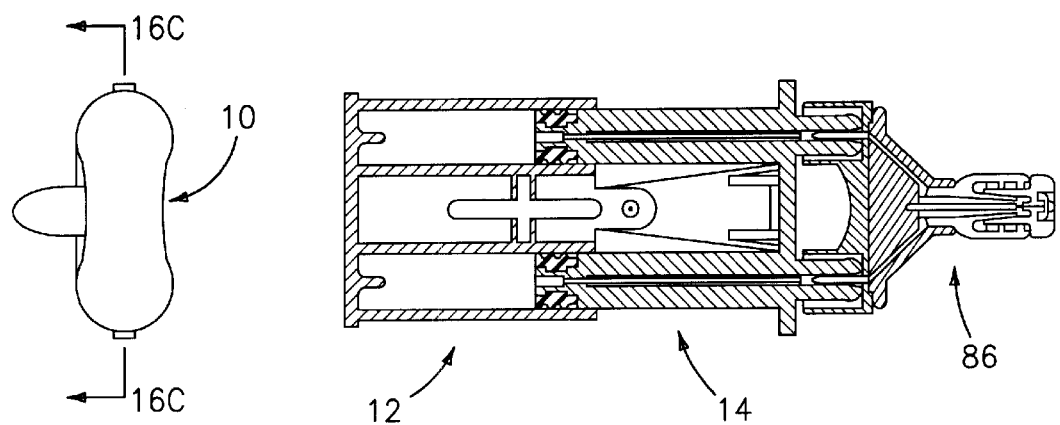
FIG. 16B  FIG. 16C
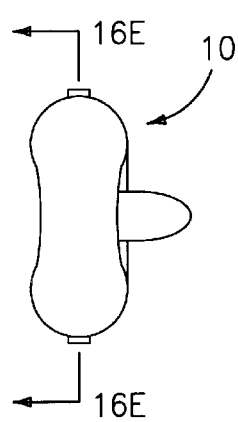 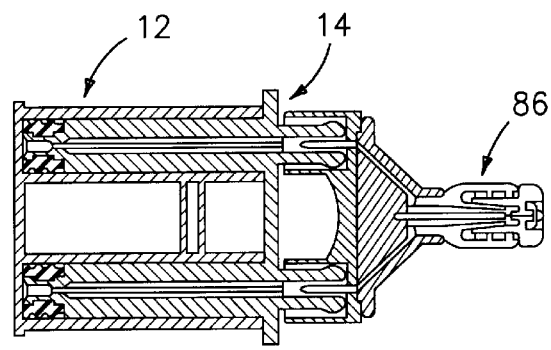
FIG. 16D  FIG. 16E

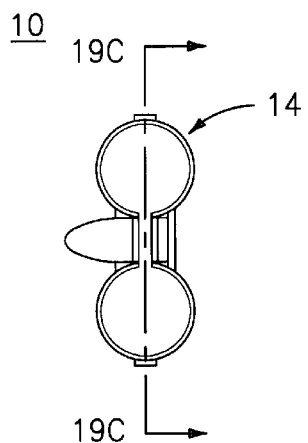
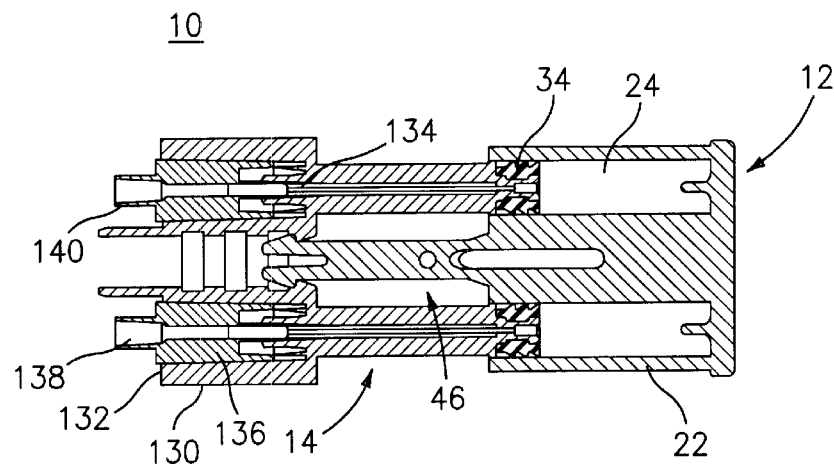
FIG. 19B
FIG. 19C
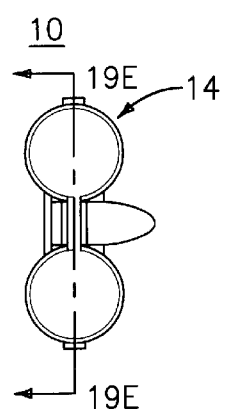
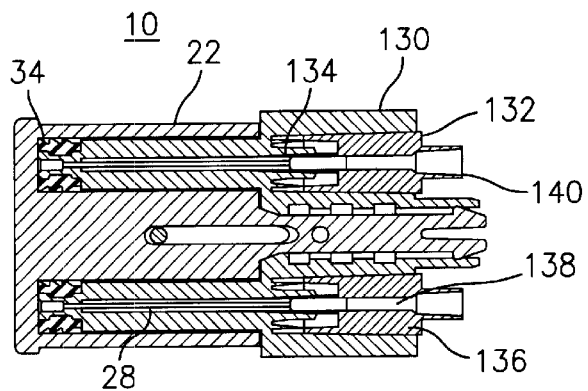
FIG. 19D
FIG. 19E

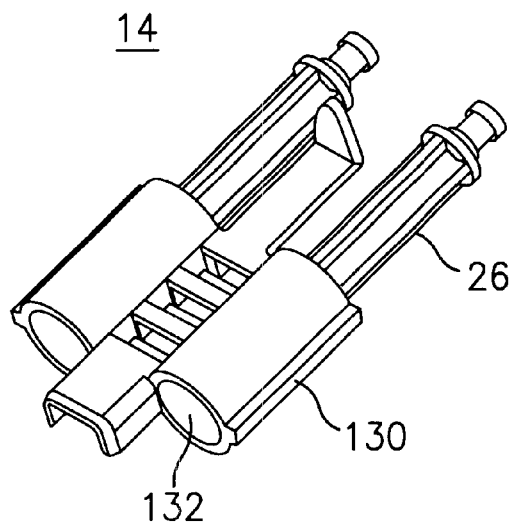
FIG. 21A
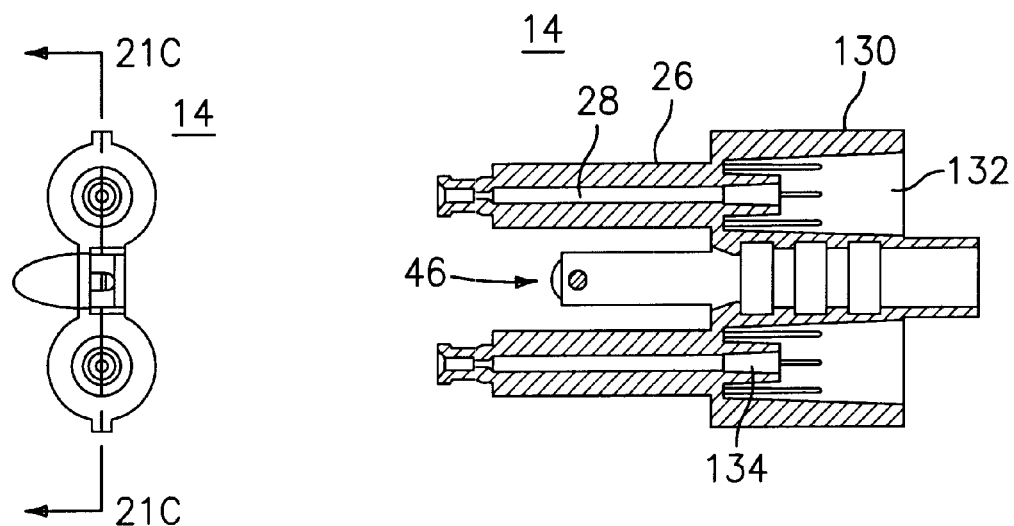
FIG. 21C
FIG. 21B

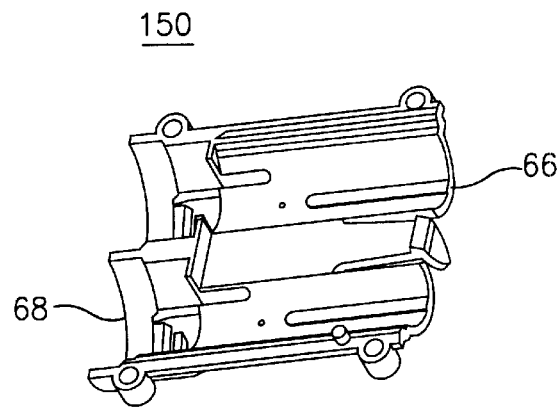
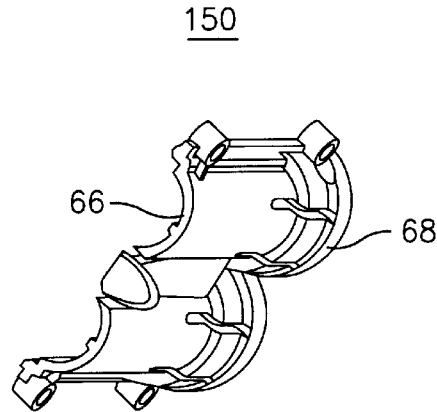
*FIG. 22A*  *FIG. 22B*
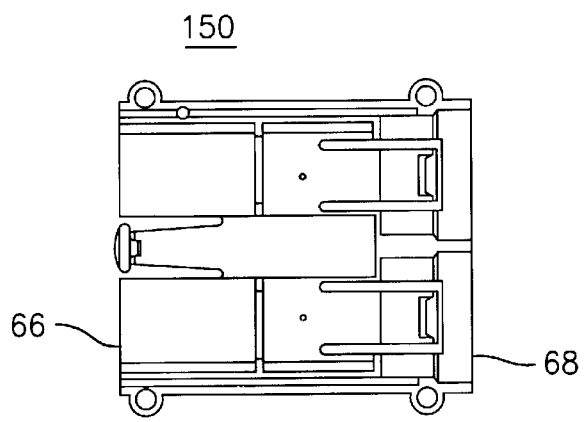
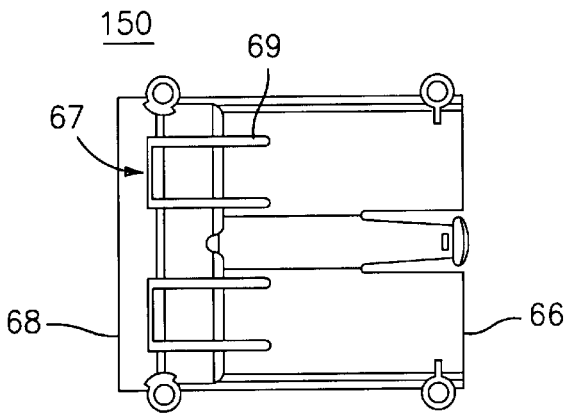
*FIG. 22C*  *FIG. 22D*

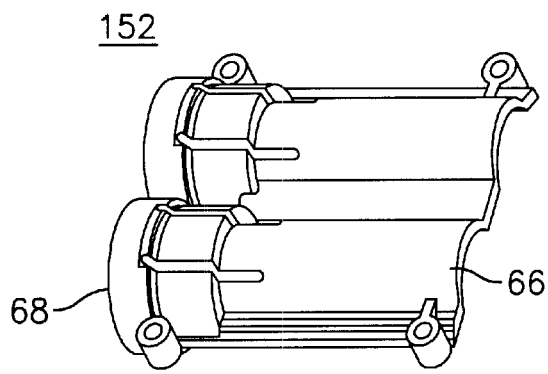
FIG. 23A
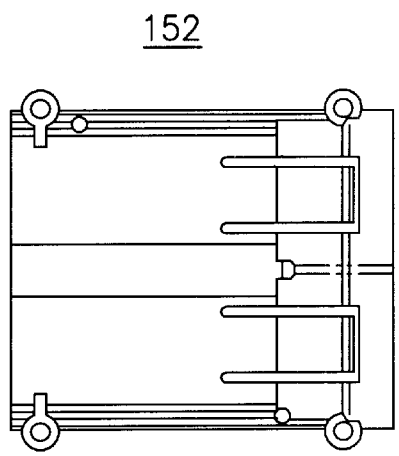 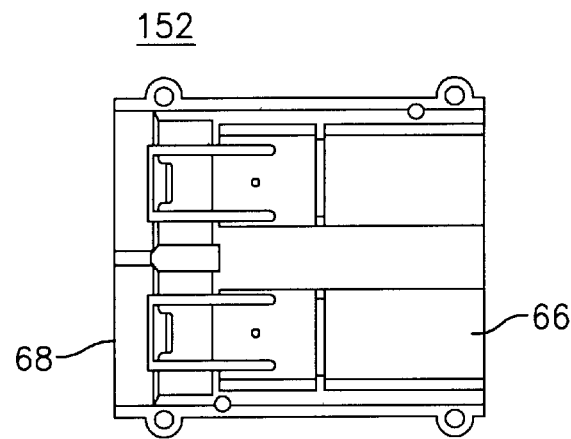
FIG. 23B          FIG. 23C

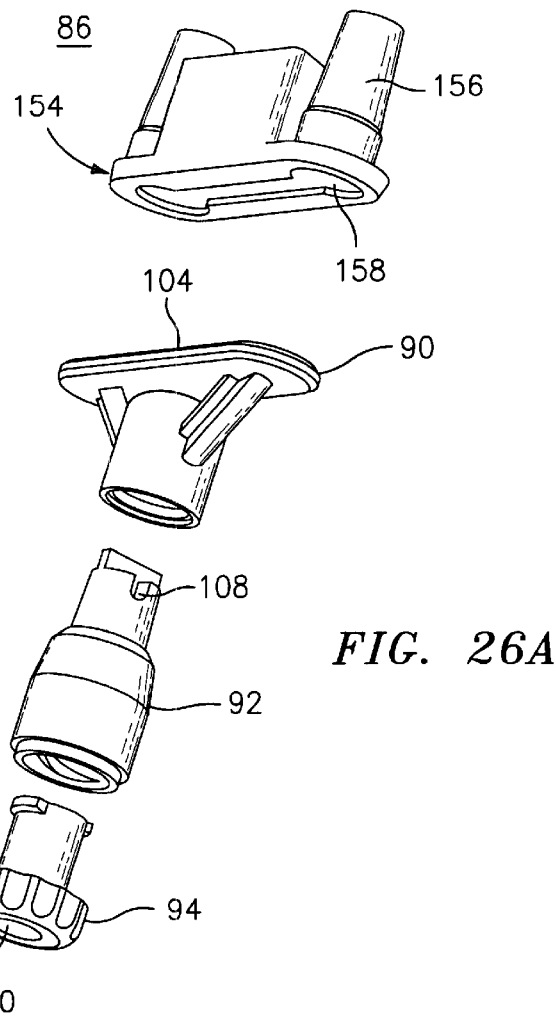
*FIG. 26A*
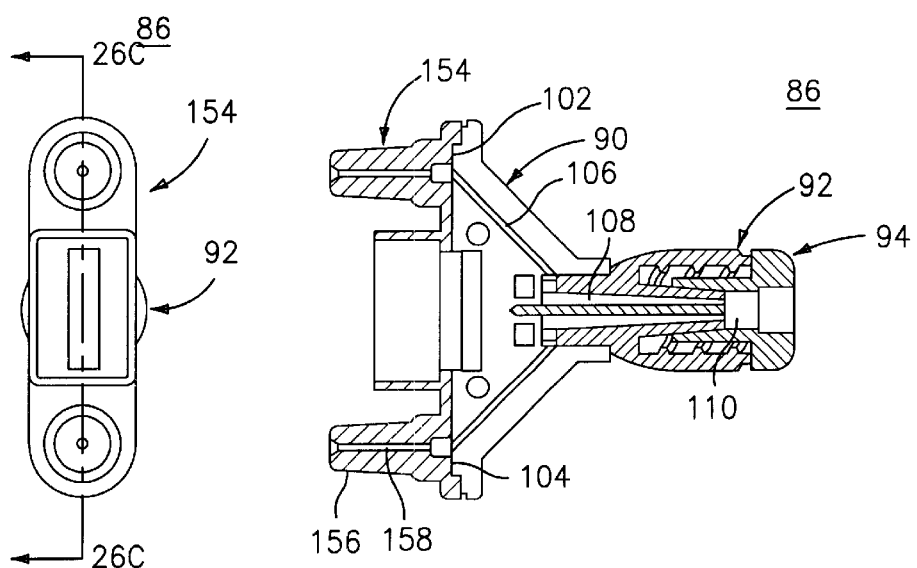
*FIG. 26B*     *FIG. 26C*

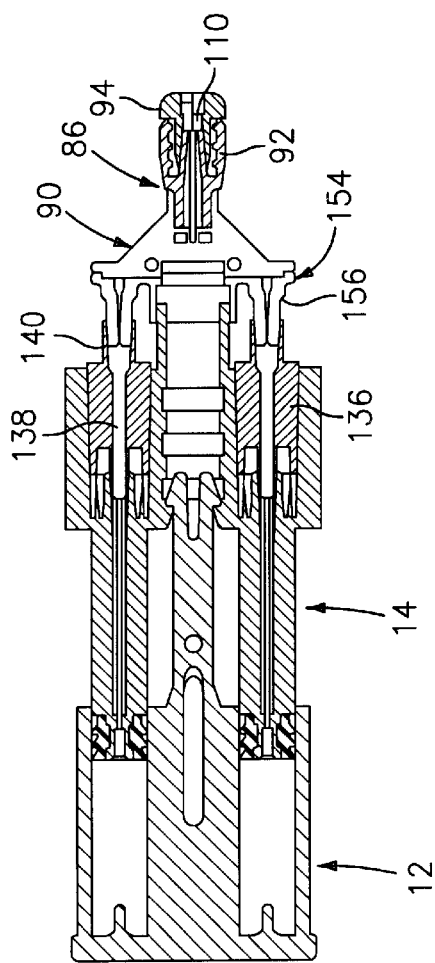
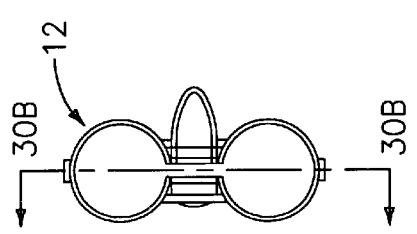
FIG. 30A
FIG. 30B
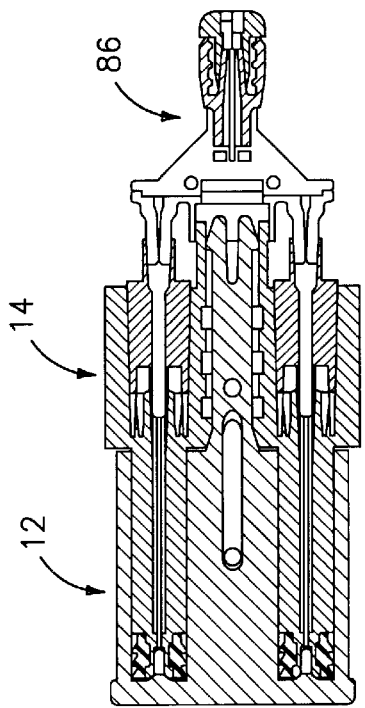
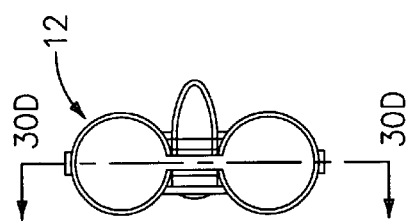
FIG. 30C
FIG. 30D

FIBRIN SEALANT APPLICATOR SYSTEM

PRIORITY

This application claims priority to a U.S. provisional application filed on Oct. 5, 1998 and having U.S. Provisional Application Serial No. 60/103,073; the contents of which are incorporated herein by reference.

BACKGROUND

1. Technical Field

The disclosure relates generally to an applicator system for applying a tissue sealant based on human or animal proteins and more particularly to an apparatus for applying an adhesive formed by combining solutions of the proteins to tissues or organs for sealing wounds or leaks, stopping bleeding and the like.

2. Description of Related Art

A fibrin sealant is a biological adhesive sealant formed by mixing two protein components, including fibrinogen and thrombin. Each protein component is derived from human plasma and is subjected to virus elimination and/or inactivation procedures. The components are typically individually dehydrated and stored in separate vials as sterile freeze-dried powders.

It is known that purified fibrinogen and thrombin, together with a variety of known adjuvants, can be combined in vitro to produce a hemostatic agent and/or a tissue sealant. Because of the rapid interaction of fibrinogen and thrombin, it is important to maintain these two blood proteins separate until applied at the application site. These protein solutions are generally delivered by devices such as a dual syringe apparatus.

One dual syringe apparatus for applying a fibrinogen-based tissue adhesive is disclosed in U.S. Pat. No. 4,359,049 to Redl et al. Redl et al. disclose a mechanism in which two standardized one-way syringes are held in a support having a common actuating means. The dispensing end of each syringe is inserted into a collection manifold where the two components are mixed. The components are then dispensed through a common needle onto the application site.

A dual syringe apparatus for the application of fibrinogen and thrombin solutions to an application site generally contain several parts, such as a syringe plunger, a "Y" manifold connector, a dispensing needle, a syringe holder, syringe needles, and conduits for transporting the solutions to the dispensing needle. Therefore, known fibrin sealant applicators, such as disclosed in U.S. Pat. No. 4,359,049 to Redl et al. discussed above, and in U.S. Pat. No. 4,874,368 to Miller et al. and U.S. Pat. No. 4,979,942 to Wolf et al. are difficult to reuse. The replenishment of the protein components typically require a combination of steps including, inter alia, removing a clip which couples the syringe plunger, removing the syringe plunger, detaching the syringes from the "Y" connector, removing the syringes from the holder, inserting new syringes, affixing the syringes to the "Y" connector, adding fibrinogen to one syringe and thrombin to another syringe, replacing the syringe plunger, replacing the plunger clip, and dispensing the solutions. In an application where time is of the essence, such a lengthy replenishing process is impractical and cumbersome.

Therefore, it would be advantageous to provide a fibrin sealant applicator system which obviates the need to replenish the solutions after the solutions have been depleted; provides for a quick and error-proof method of usage; keeps the solutions within air-sealed compartments prior to usage to prevent air from mixing with the solutions; and is economical.

SUMMARY

Fibrin sealant applicator systems are provided for dispensing a first and a second protein solution to form a biological adhesive which overcome the disadvantages of the prior art. The first and second protein solutions are preferably fibrinogen and thrombin solutions which may intermix on an application site or within the applicator to form a fibrin sealant. The fibrin sealant applicator systems according to the present disclosure include two piston-type sub-assemblies coupled to two vials storing the fibrinogen and thrombin via a coupling unit. The piston-type sub-assemblies store sterilized water within reservoirs which are in fluid communication with the vials via the coupling unit. The water is forced into the vials to form the fibrinogen and thrombin solutions. The solutions are then drawn into the reservoirs and a Y-coupler is attached to the distal end of the piston-type sub-assemblies. The Y-coupler provides fluid communication between the reservoirs and a nozzle body for dispensing the solutions when distal pressure is created within the reservoirs to force the solutions towards the nozzle body.

BRIEF DESCRIPTION OF THE DRAWINGS

Various embodiments are described herein with reference to the drawings, wherein:

FIGS. 1–18 illustrate the components and method of operation of a fibrin sealant applicator in accordance with a first embodiment of the present disclosure wherein:

FIG. 2A is a perspective view of two cylindrical reservoirs of the sub-assemblies shown by FIGS. 1A–1E;

FIG. 2B is a bottom plan view of the two cylindrical reservoirs shown by FIG. 2A;

FIG. 2C is a cross-sectional view of the two cylindrical reservoirs taken along line A—A in FIG. 2B;

FIG. 10A is an assembly view showing coupling of the two piston-type sub-assemblies, the loading unit, and the vials;

FIG. 10B is top plan view of the components shown by FIG. 10A;

FIG. 10C is a cross-sectional view of the components shown by FIG. 10A taken along line A—A in FIG. 10B;

FIG. 11B is a top plan view of the Y-couple shown by FIG. 11A;

FIG. 11C is a cross-sectional view of the Y-coupler shown by FIG. 11A taken along line A—A in FIG. 11B;

FIG. 11D is a cross-sectional view of the Y-coupler shown by FIG. 11A taken along line C—C in FIG. 11C;

FIG. 14A is a perspective view of a collar of the Y-coupler shown by FIG. 11A;

FIG. 14B is a side view of the collar shown by FIG. 14A;

FIG. 14C is a cross-sectional view of the collar shown by FIG. 14A taken along line A—A in FIG. 14B;

FIG. 15A is a perspective view of a nozzle body of the Y-coupler shown by FIG. 11A;

FIG. 15B is a top plan view of the nozzle body shown by FIG. 15A;

FIG. 16A is an assembly view of coupling the two piston-type subassemblies and the Y-coupler;

FIG. 16B is a top plan view of the assembled components shown by FIG. 16A with the piston-type sub-assemblies in the open configuration;

FIG. 16C is a cross-sectional view of the assembled components shown by FIG. 16B taken along line A—A in FIG. 16B;

FIG. 16D is a top plan view of the assembled components shown by FIG. 16A with the piston-type sub-assemblies in the closed configuration;

FIG. 16E is a cross-sectional view of the assembled components shown by FIG. 16D taken along line A—A in FIG. 16D;

FIGS. 19–30 illustrate the components and method of operation of a fibrin sealant applicator in accordance with a second embodiment of the present disclosure wherein:

FIG. 19B is a top plan view of the two piston-type sub-assemblies shown by FIG. 19A in an open configuration;

FIG. 19C is a cross-sectional view of the two piston-type sub-assemblies taken along line A—A in FIG. 19B;

FIG. 19D is a top plan view of the two piston-type sub-assemblies shown by FIG. 19A in a closed configuration;

FIG. 19E is a cross-sectional view of the two piston-type sub-assemblies taken along line A—A in FIG. 19D;

FIG. 21A is a perspective view of two pistons of the sub-assemblies shown by FIGS. 19A–19E;

FIG. 21B is a bottom plan view of the two pistons shown by FIG. 21A;

FIG. 21C is a cross-sectional view of the two pistons taken along line A—A in FIG. 21B;

FIGS. 22A and 22B are perspective views of the bottom portion of a loading unit;

FIG. 22C is a top plan view of one side of the bottom portion shown by FIGS. 22A and 22B;

FIG. 22D is a top plan view of an opposite side of the bottom portion shown by FIGS. 22A and 22B;

FIG. 23A is a perspective view of the top portion of the loading unit;

FIG. 23B is a top plan view of one side of the top portion shown by FIG. 23A;

FIG. 23C is a top plan view of an opposite side of the top portion shown by FIG. 23A;

FIG. 26A is an exploded of a Y-coupler;

FIG. 26B is a top plan view of the Y-couple shown by FIG. 26A;

FIG. 26C is a cross-sectional view of the Y-coupler shown by FIG. 26A taken along line A—A in FIG. 26B;

FIG. 30A is a top plan view of the piston-type sub-assemblies in the open configuration coupled to the Y-coupler;

FIG. 30B is a cross-sectional view of the assembled components shown by FIG. 30A taken along line A—A in FIG. 30A;

FIG. 30C is a top plan view of the piston-type sub-assemblies in the closed configuration coupled to the Y-coupler; and FIG. 30D is a cross-sectional view of the assembled components shown by FIG. 30C taken along line A—A in FIG. 30C.

DETAILED DESCRIPTION OF PREFERRED EMBODIMENTS

Figure 1A:
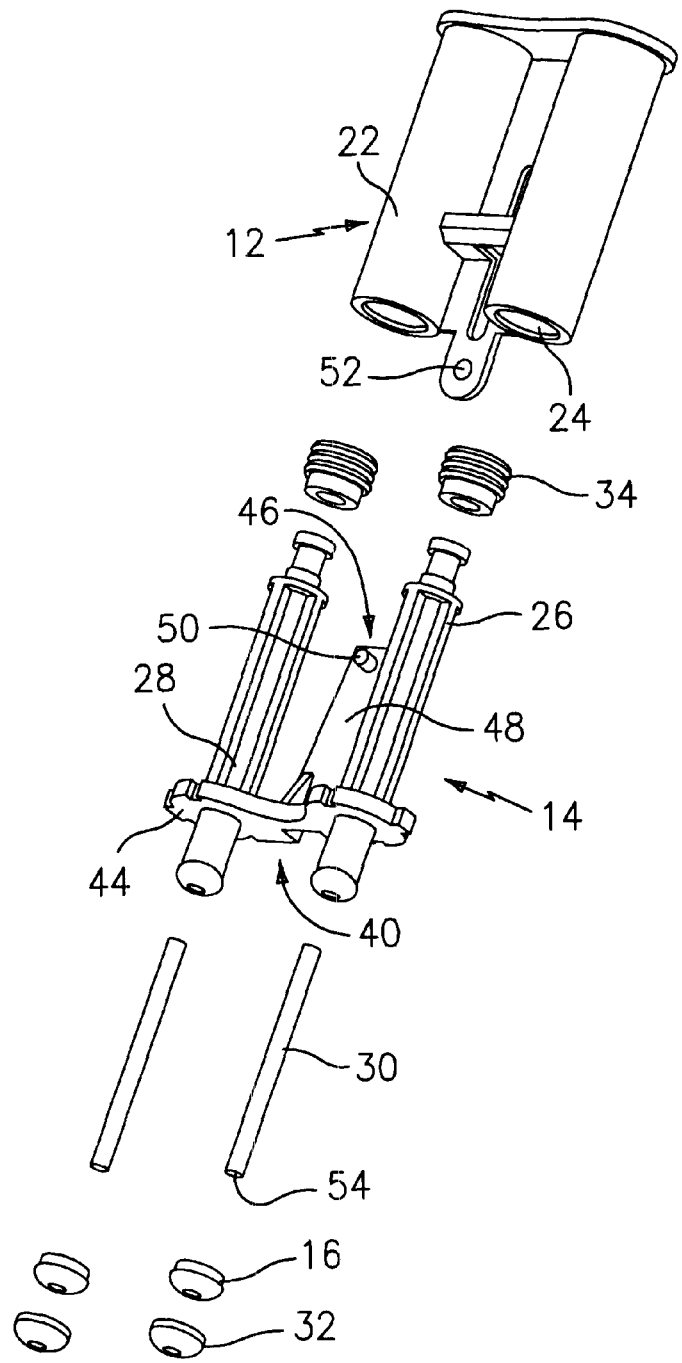
FIG. 1A is an exploded view of two piston-type sub-assemblies.
Figure 1D:
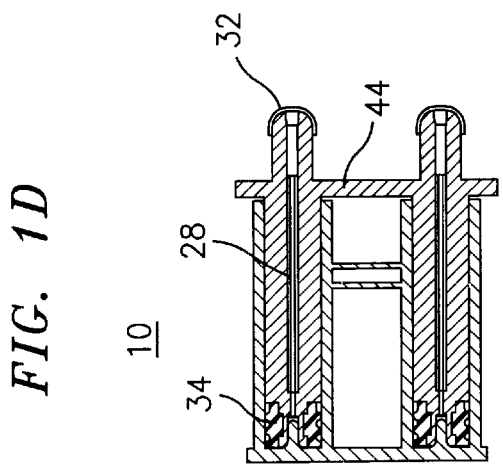
FIG. 1D is a top plan view of the two piston-type sub-assemblies shown by FIG. 1A in a closed configuration.
Figure 1E:
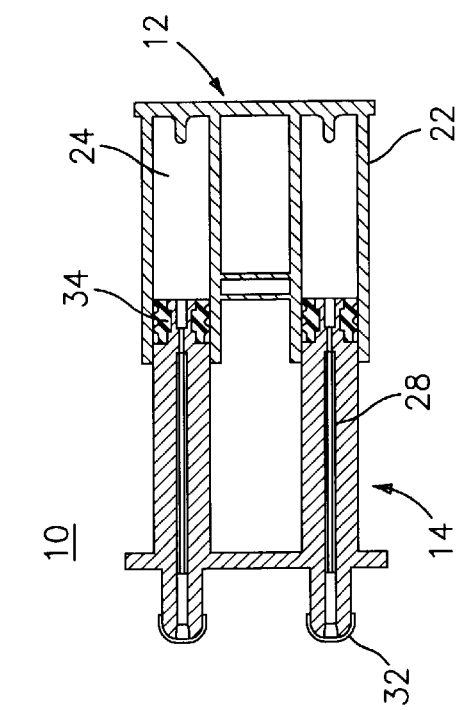
FIG. 1E is a cross-sectional view of the two piston-type sub-assemblies taken along line A—A in FIG. 1D.
Figure 1B:
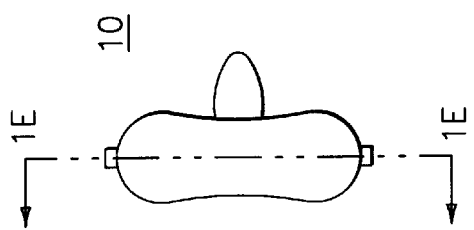
FIG. 1B is a top plan view of the two piston-type sub-assemblies shown by FIG. 1A in an open configuration.
Figure 1C:
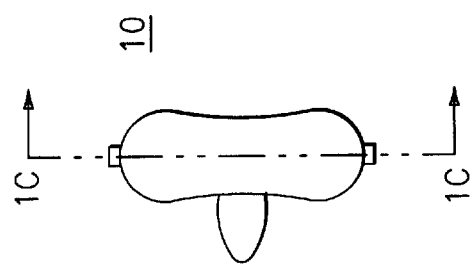
FIG. 1C is a cross-sectional view of the two piston-type sub-assemblies taken along line A—A in FIG. 1B.
Figure 3A:
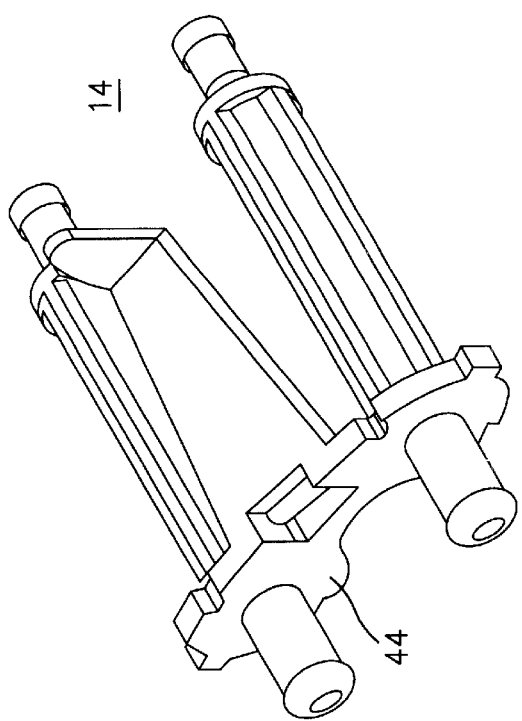
FIG. 3A is a perspective view of two pistons of the sub-assemblies shown by FIGS. 1A–1E.
Figure 3C:
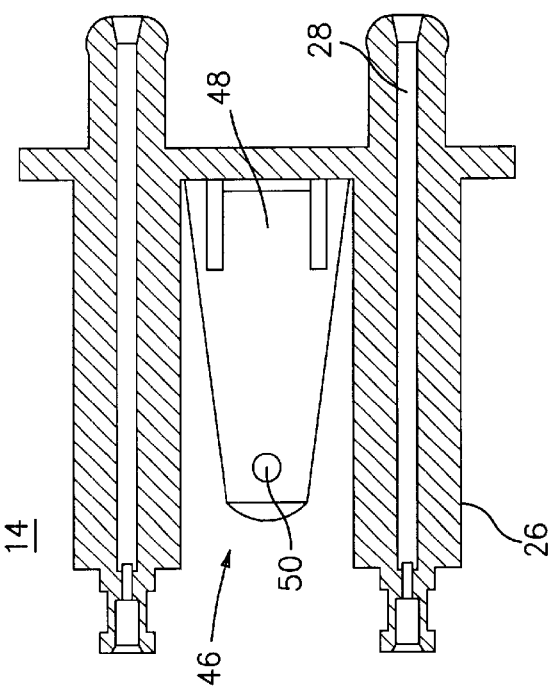
FIG. 3C is a cross-sectional view of the two pistons taken along line A—A in FIG. 3B.
Figure 3B:
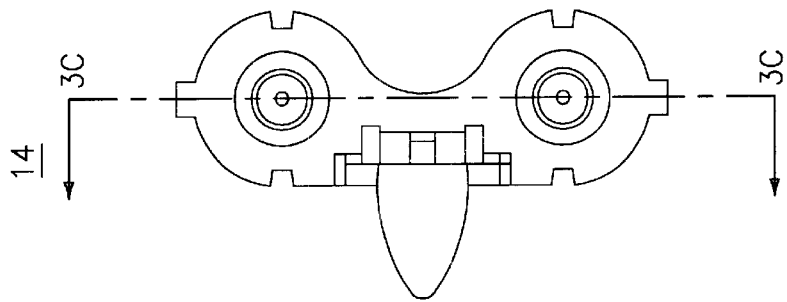
FIG. 3B is a bottom plan view of the two pistons shown by FIG. 3A.

Two embodiments of a fibrin sealant applicator system are described herein below in conjunction with FIGS. 1A–30D. With reference to FIGS. 1A–18C, the components and method of operation of the first embodiment of the fibrin sealant applicator system are described. With reference to FIGS. 19A–30D, the components and method of operation of the second embodiment of the fibrin sealant applicator system are described. The fibrin sealant applicator system embodiments described herein below are preferably manufactured from biodegradable plastics and other materials. In their preferred embodiments, both are packaged as a kit and used only once to apply a solution of fibrinogen and a solution of thrombin to an application site.

Referring to FIGS. 1–10, the components used during the formation and loading of the fibrinogen and thrombin solutions to the first embodiment of the fibrin sealant applicator system will now be described. For this purpose, the fibrin sealant applicator system includes two piston-type sub-assemblies 10 (FIGS. 1A–1E) coupled together and each having a reservoir assembly 12 (FIGS. 2A–2C), a piston assembly 14 (FIGS. 3A–3C), a septum 16 (FIGS. 4A–4B); and a coupling unit 18 (FIGS. 6A–6D and 7A–7C) having two hollow needles 20 (FIGS. 8A–8C and 9A–9E) therein.

Each reservoir assembly 12 includes a cylindrical reservoir 22 having a compartment 24 for storing sterilized water therein. The sterilized water is preferably stored within compartment 24 of each reservoir 22 during manufacturing and hermetically sealed therein to prevent contamination thereof. Each reservoir assembly 12 is preferably made from polypropylene.

Figure 4A:
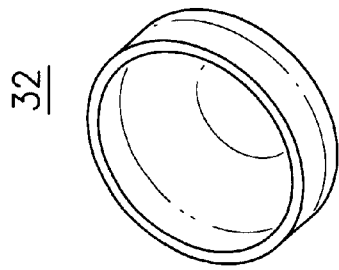
FIG. 4A is a perspective view of a septum for sealing a distal end of each piston shown by FIGS. 3A–3C.
Figure 4B:
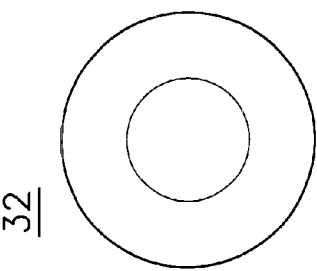
FIG. 4B is a top view of the septum shown by FIG. 4A.
Figure 6A:
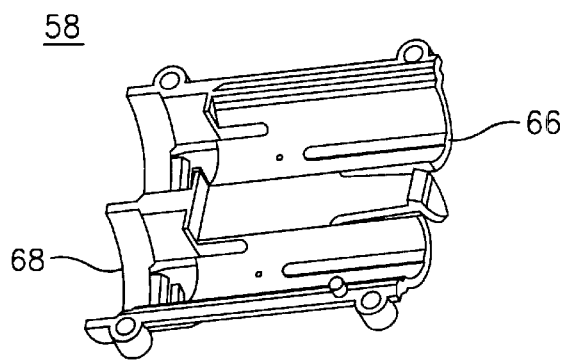
FIGS. 6A and 6B are perspective views of the bottom portion of a loading unit.
Figure 6B:
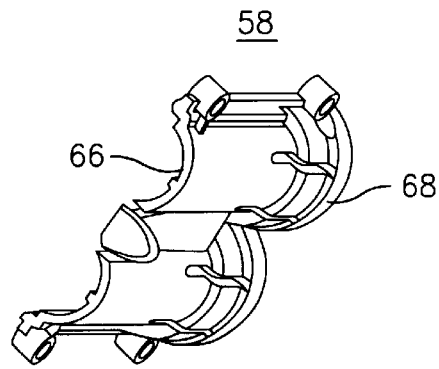
Figure 6C:
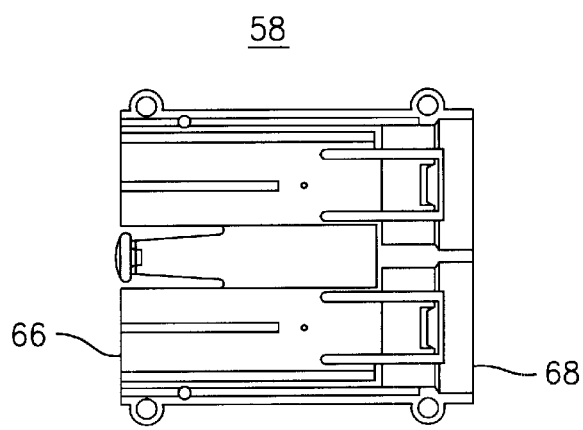
FIG. 6C is a top plan view of one side of the bottom portion shown by FIGS. 6A and 6B.
Figure 6D:
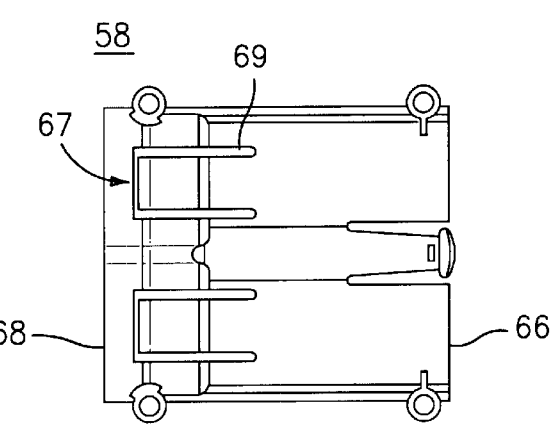
FIG. 6D is a top plan view of an opposite side of the bottom portion shown by FIGS. 6A and 6B.
Figure 7A:
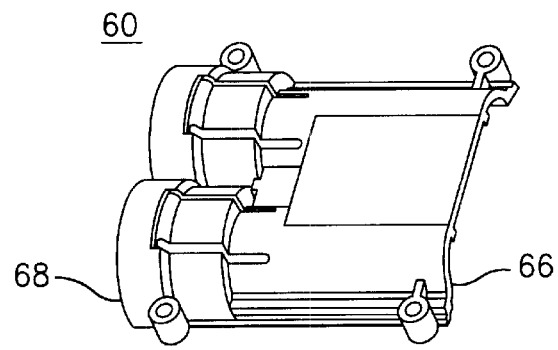
FIG. 7A is a perspective view of the top portion of the loading unit.
Figure 7B:
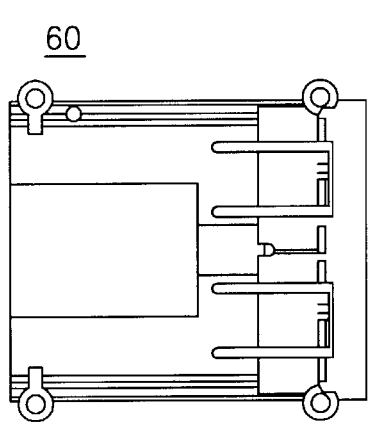
FIG. 7B is a top plan view of one side of the top portion shown by FIG. 7A.
Figure 7C:
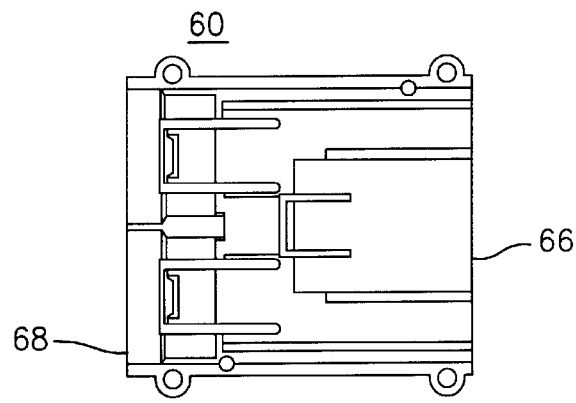
FIG. 7C is a top plan view of an opposite side of the top portion shown by FIG. 7A.
Figure 8A:
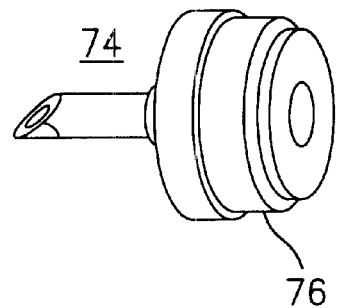
FIG. 8A is a perspective view of a hollow needle.
Figure 8B:
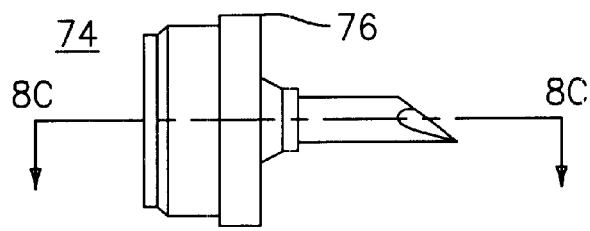
FIG. 8B is a side view of the hollow needle shown by FIG. 8A.
Figure 8C:
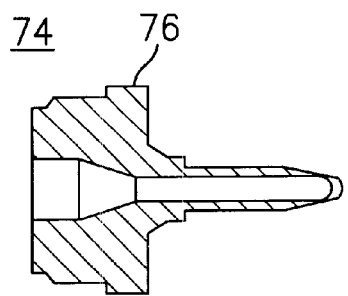
FIG. 8C is a cross-sectional view of the hollow needle shown by FIG. 8A taken along line A—A in FIG. 8B.
Figure 9A:
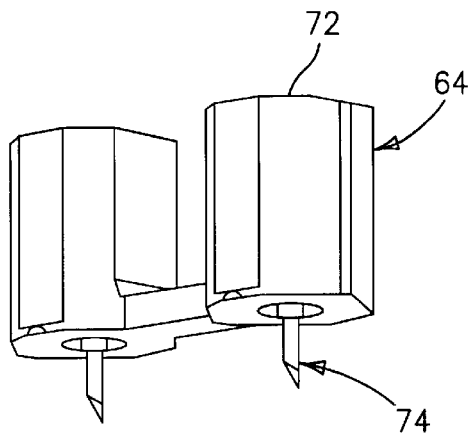
FIG. 9A is a perspective view of the hollow needle placed within a shuttle of the loading unit for piercing a seal on a vial inserted within the loading unit.
Figure 9B:
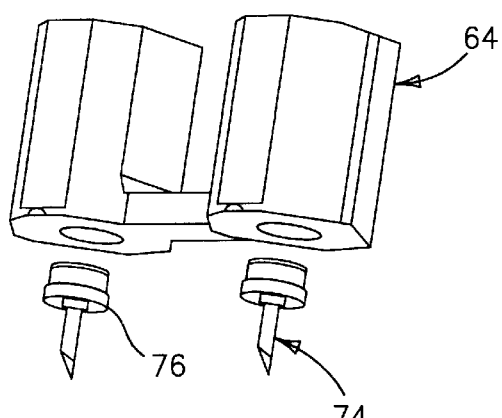
FIG. 9B is an assembly view of the hollow needle shown by FIG. 9A being placed within the shuttle.
Figure 9C:
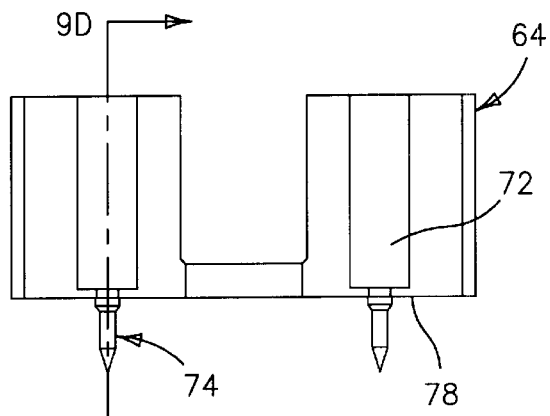
FIG. 9C is a side view of the hollow needle-shuttle assembly.
Figure 9D:
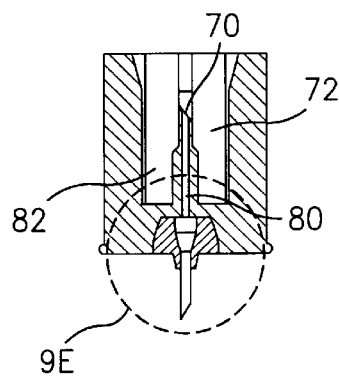
FIG. 9D is a cross-sectional view of the hollow needle-shuttle assembly shown by FIG. 9C taken along line A—A in FIG. 9C.
Figure 9E:
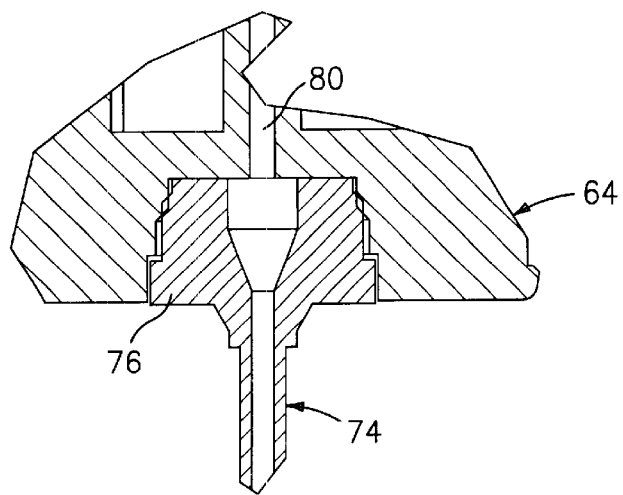
FIG. 9E is an enlarged view of the area of detail indicated by arrow "B" in FIG.9D.

Each piston assembly 14 includes a piston 26 having a bore 28 therethrough (FIGS. 3A–3C), an elongated cylindrical tube 30 extending through bore 28, a distal seal 32, and a proximal seal 34. Each piston assembly 14 is preferably made from polypropylene and distal and proximal seals 32 and 34 are preferably made from silicone. Distal seal 32, as shown by FIGS. 4A–4B, is semi-spherical in shape and configured to matingly engage seal 16. Distal seal 32 and seal 16 are then attached to the distal end of piston assembly 14 as shown by FIG. 1A to prevent contaminants from entering the two piston-type sub-assemblies 10.

Figure 5A:
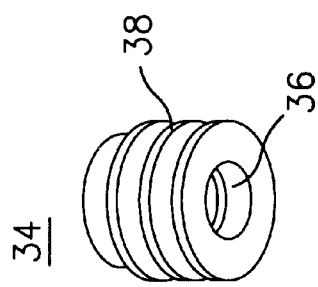
FIG. 5A is a perspective view of a seal for connection to a proximal end of each piston shown by FIGS. 3A–3C.
Figure 5C:
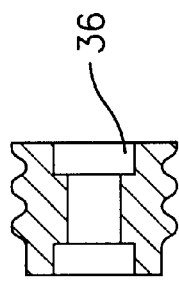
FIG. 5C is a cross-sectional view of the seal shown by FIG. 5A taken along line A—A in FIG. 5B.
Figure 5B:
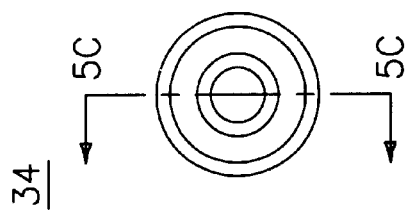
FIG. 5B is a bottom plan view of the seal shown by FIG. 5A.

Proximal seal 34, as shown by FIGS. 5A–5C, is cylindrical in shape having a bore 36 therethrough and threads 38 on an inner and outer surface. Proximal seal 34 is configured for placement on a proximal end of piston assembly 14 to wedge the proximal end of piston 26 within compartments 24 as shown by FIG. 1A. Distal and proximal seals 32 and 34 prevent contaminants from entering the piston-type sub-assemblies and compromising the sterility of the sterile water within compartment 24 of each reservoir 22.

A connecting mechanism 40 connects each piston assembly 14. Connecting mechanism 42 includes a hatch-bar 44 having a finger-controlled locking assembly 46. Locking assembly 46 includes a rest bar 48 having tab 50 protruding therefrom. Rest bar 48 moves from an unlocked position to a locked position to move tab 50 to matingly engage a hole 52 (FIGS. 1A and 2A) on reservoir assembly 12 to lock reservoir assembly 12 to piston assembly 14. This prevents reservoirs 22 from being inadvertently moved distally or pushed against pistons 26. When the solutions are ready to be dispensed, the operator can use a finger to lift rest bar 48 to disengage tab 50 from within hole 52. Accordingly, locking assembly 46 is unlocked, thereby allowing free movement of reservoir assembly 12 along the longitudinal axis of piston assembly 14. It is contemplated to design locking assembly 46 to also provide a locking function when reservoir assembly 12 has been moved distally towards piston assembly 14 to prevent proximal movement of reservoir assembly 12.

With reference to FIGS. 1C, 1E and 10A–10I, each reservoir 22 is in fluid communication with the distal end of corresponding piston 26 via bore 54 extending within tube 30. It is contemplated to size bore 54 to allow for little or no water to remain therein when dispensing the sterilized water to vials containing powdered fibrinogen and thrombin, as further described below.

A coupling unit 56 (FIGS. 6A–6D and 7A–7C) having body half portions 58 and 60 acts as an interface between piston-type sub-assemblies 10 and vials 62 (See FIGS. 10A–10I). Coupling unit 56 includes molded compartments therein for fitting vials 62 and a shuttle 64. Coupling unit 56 includes a proximal interface 66 for receiving and coupling to the two piston-type sub-assemblies 10 and a distal interface 68 for receiving and coupling to vials 62 storing fibrinogen and thrombin. Vials 62 are inserted within distal interface 68 and are coupled to the coupling unit by a coupling mechanism 67. Coupling mechanism 67 includes flexible tabs 69 which flex outwardly as vials 62 are inserted within distal interface 68 and then flex back to grip the neck of vials 62 and hold them in place. Body half portions 58 and 60 of the coupling unit 56 are preferably made from ABS plastics.

With reference to FIGS. 9A–9E, shuttle 64 includes two proximal hollow needles 70 within recess 72 for piercing septum 16 and distal seal 32 when the two piston-type sub-assemblies 10 are inserted within proximal interface 66. Recess 72 is configured to matingly engage the distal end of pistons 26 and to securely connect coupling unit 56 with the two piston-type sub-assemblies 10. The distal hollow needles 74 (FIGS. 8A–8C and 9A–9E) having a base 76 are matingly engaged to distal recesses 78 on shuttle 64 (FIGS. 10A–10I) for piercing a seal overlaying vials 62. Proximal hollow needles 70, distal hollow needles 74, and bores 80 within shuttle 64 form passageways 82 for providing fluid communication between the distal end of piston assembly 14 and vials 62 as shown by FIGS. 9D, 9E, 10C, 10E, 10G and 10I.

Shuttle 64 is capable of moving between tabs 84 within coupling unit 56 and hatch-bar 44 of the piston assembly 14. Therefore, in order to prevent inadvertent piercing of the seal overlaying vials 62, shuttle 64 is kept positioned near proximal interface 66 of coupling unit 56 until the operator is ready to form the solutions.

Figures 10D, 10E:
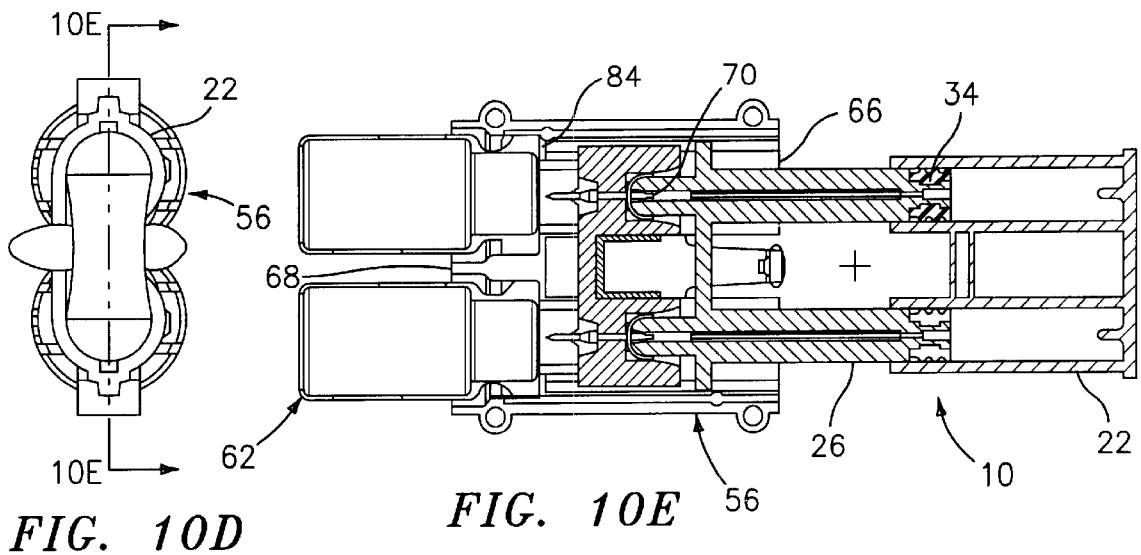
FIG. 10D is a top plan view of the assembled components shown by FIG. 10A with the shuttle in a non-piercing position and the piston-type sub-assemblies in the open configuration.
FIG. 10E is a cross-sectional view of the assembled components shown by FIG. 10D taken along line A—A in FIG. 10D.
Figures 10F, 10G:
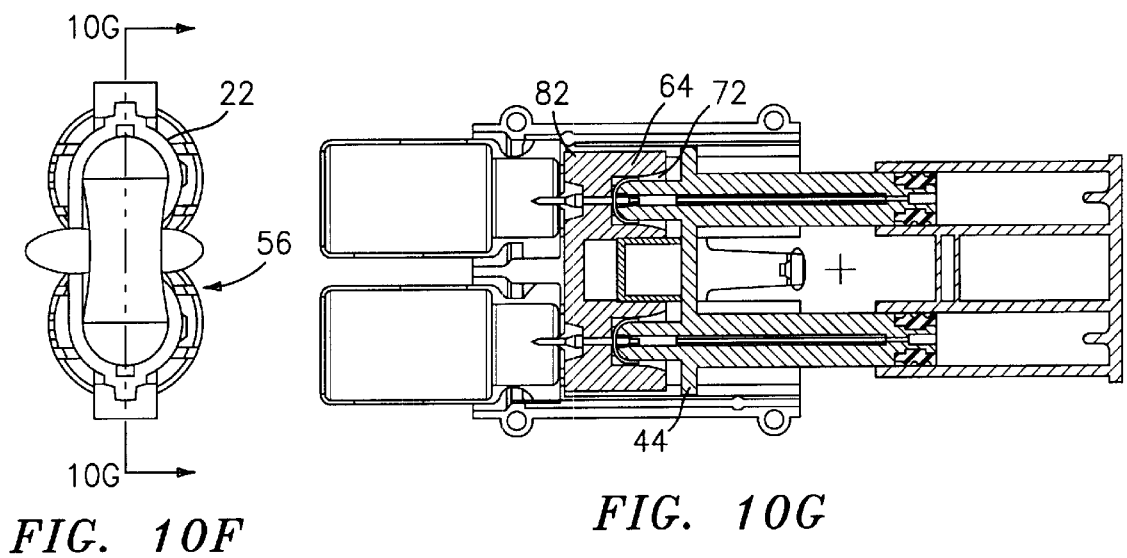
FIG. 10F is a top plan view of the assembled components shown by FIG. 10A with the shuttle in a piercing position and the piston-type sub-assemblies in the open configuration.
FIG. 10G is a cross-sectional view of the assembled components shown by FIG. 10F taken along line A—A in FIG. 10F.
Figures 10H, 10I:
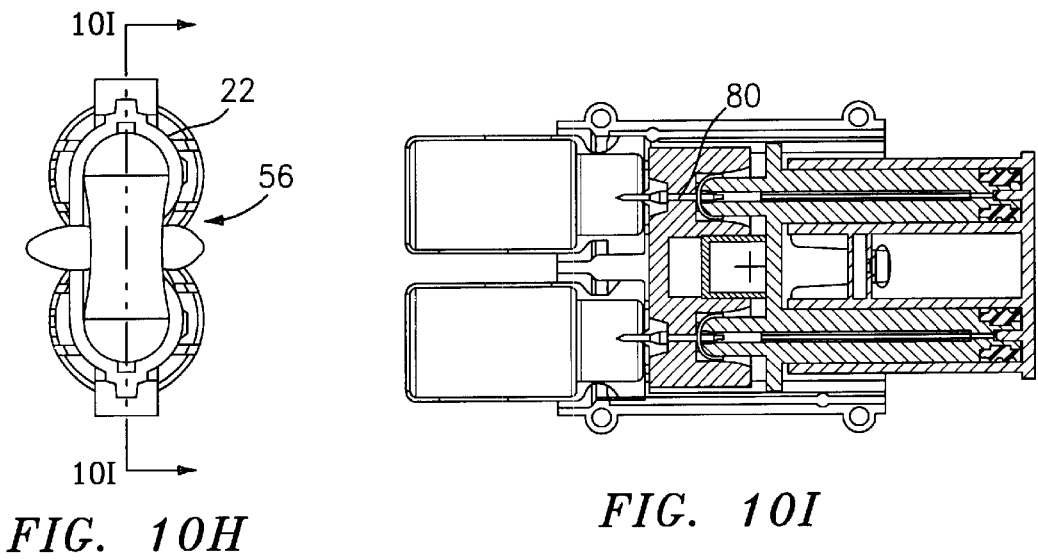
FIG. 10H is a top plan view of the assembled components shown by FIG. 10A with the shuttle in the piercing position and the piston-type sub-assemblies in the closed configuration.
FIG. 10I is a cross-sectional view of the assembled components shown by FIG. 10H taken along line A—A in FIG. 10H.
Figure 11A:
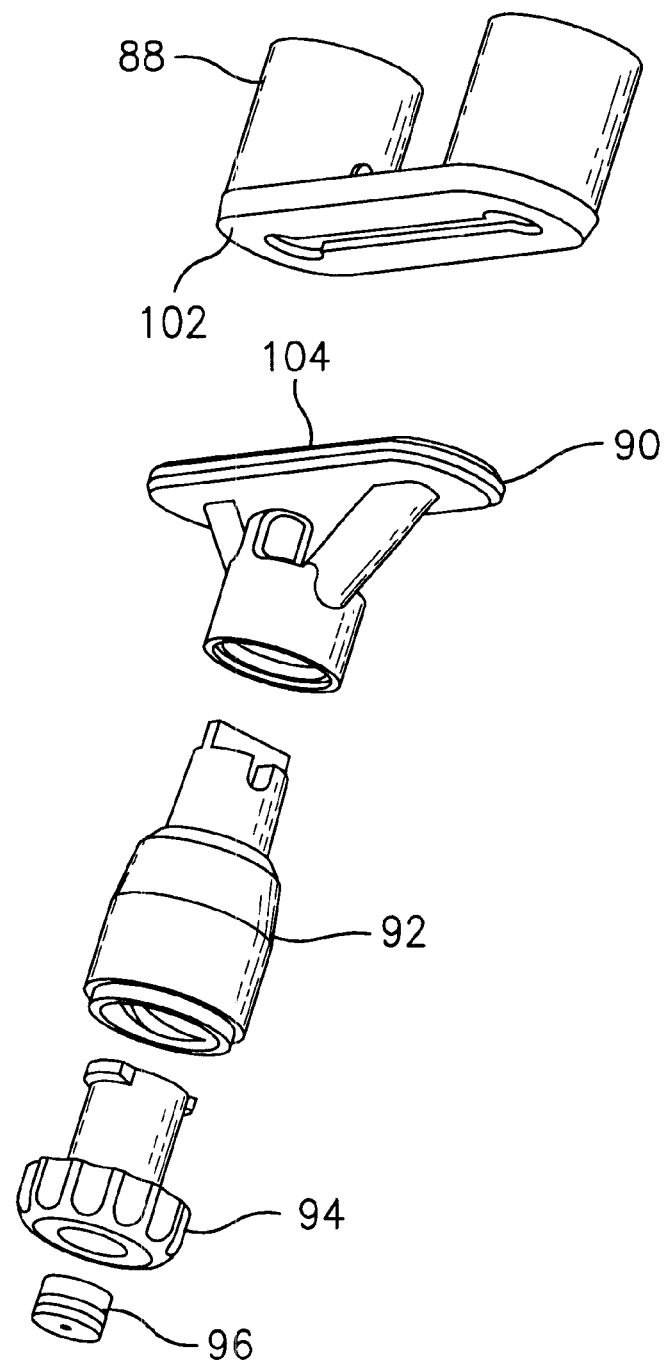
FIG. 11A is an exploded of a Y-coupler.

With reference to FIGS. 10D–10I, the solutions are formed by moving shuttle 64 distally from a non-piercing position to a piercing position in order for needles 74 to pierce the seal overlaying vials 62 (FIG. 10G). Distal holding needles 74 are preferably made from nylon. Reservoir assembly 12 is then moved distally to decrease the volumetric capacity within compartments 24 to force the sterilized water therein to flow distally through bores 54 of tubes 30 (FIG. 10I). The water flows through bores 54 and passageways 82 into vials 62. The entire assembly is then shaken to thoroughly mix the water with the powdered fibrinogen and thrombin to form the solutions. Reservoir assembly 12 is then moved proximally away from piston assembly 14 creating proximal pressure within the reservoirs 22 to draw the solutions from vials 62 to reservoirs 22.

When the solutions have been drawn into reservoirs 22, shuttle 64 is moved proximally to remove needle 74 from within vials 62. Vials 62 are then removed from distal interface 68 of coupling unit 56. Coupling unit 56 is subsequently removed from the two piston-type sub-assemblies 10 and a Y-coupler dispensing unit assembly 86 (FIGS. 11A–11D) is then coupled to the two piston-type sub-assemblies 10 as shown in FIGS. 16A–16E.

Figure 12A:
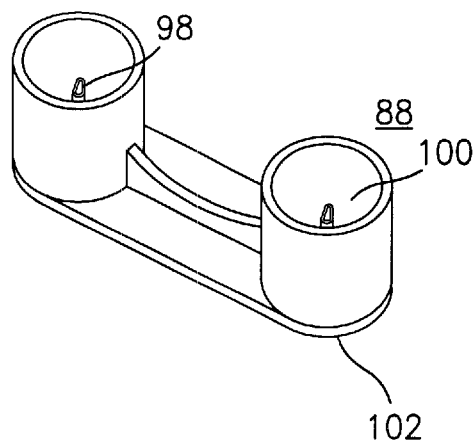
FIG. 12A is a perspective view of an adaptor of the Y-coupler shown by FIG. 11A.
Figure 12B:
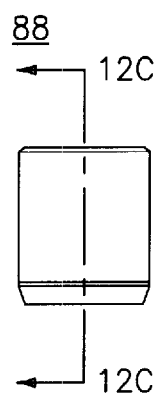
FIG. 12B is a side view of the adaptor shown by FIG. 12A.
Figure 12C:
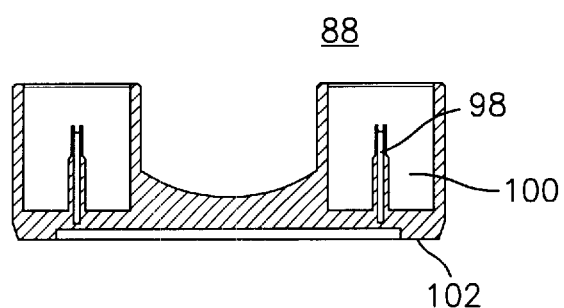
FIG. 12C is a cross-sectional view of the adaptor shown by FIG. 12A taken along line A—A in FIG. 12B.

Y-coupler dispensing unit assembly 86 includes an adapter 88, a body tip 90, a collar 92, a nozzle body 94, and a seal 96. The components are assembled together as shown by FIGS. 11A–11D to form Y-coupler dispensing unit assembly 86. Adapter 88 includes two hollow needles 98 recessed within cavities 100 to prevent accidental piercing or pricking of an operator's finger (FIGS. 12A–12C). Hollow needles 98 matingly engage seal 16 and distal seal 32 at the distal end of piston assembly 14 to provide fluid communication between reservoirs 22 and distal face 102 of adapter 88. Adapter 88 and body tip 90 are preferably made from polypropylene. Alternatively, adapter 88 and body tip 90 are made from ABS plastics. Collar 92 and nozzle body 94 are preferably made from ABS plastics.

Figure 13A:
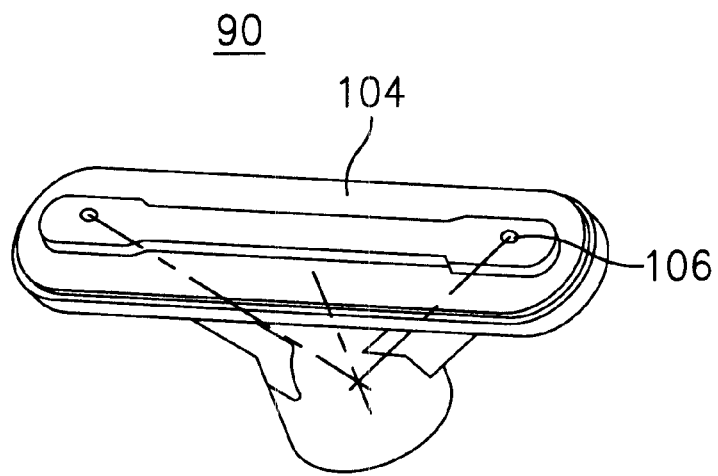
FIG. 13A is a perspective view of a body tip of the Y-coupler shown by FIG. 11A.
Figure 13B:
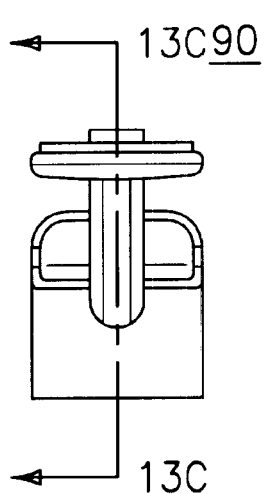
FIG. 13B is a side view of the body tip shown by FIG. 13A.
Figure 13C:
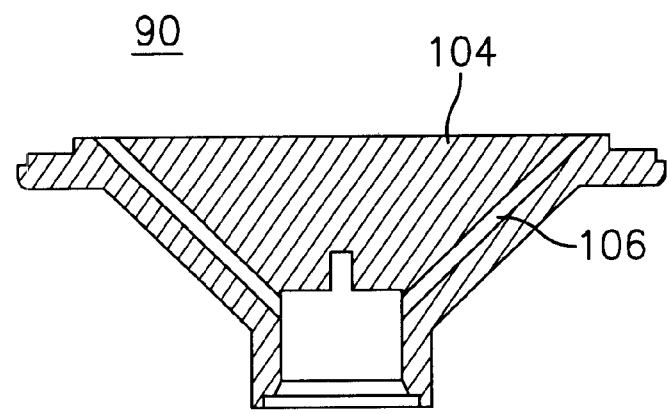
FIG. 13C is a cross-sectional view of the body tip shown by FIG. 13A taken along line A—A in FIG. 13B.
Figure 17A:
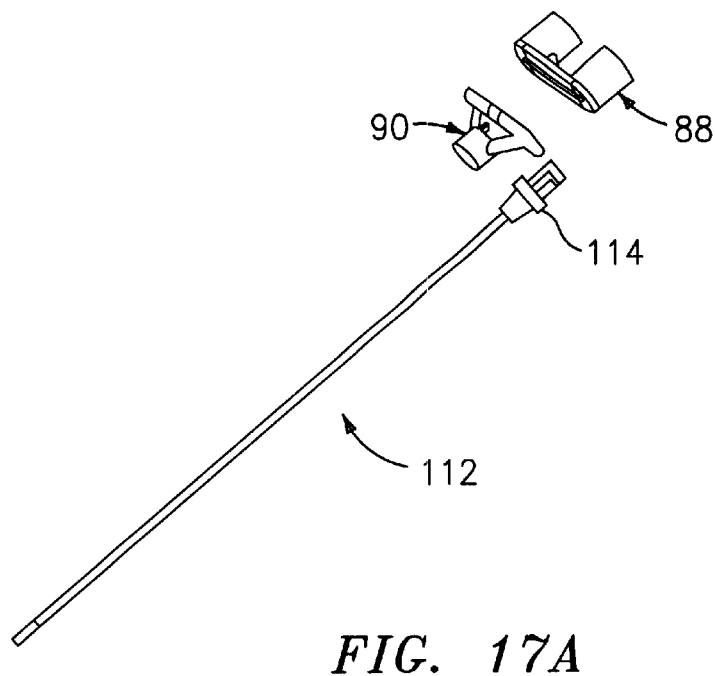
FIG. 17A is a perspective view of the components of a laparoscopic tip 20 assembly configured for coupling to the two piston-type sub-assemblies shown by FIG. 1A.
Figure 17B:
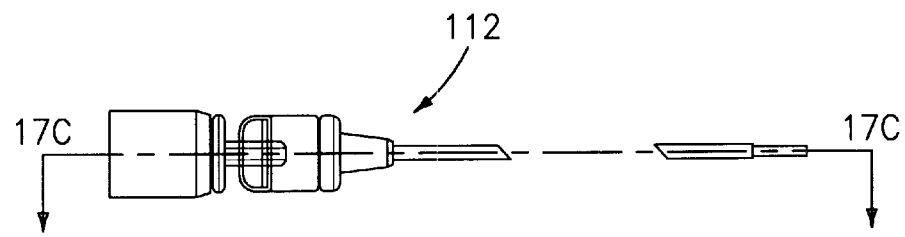
FIG. 17B is a side view of the assembled components of the laparoscopic tip assembly shown by FIG. 17A.
Figure 17C:
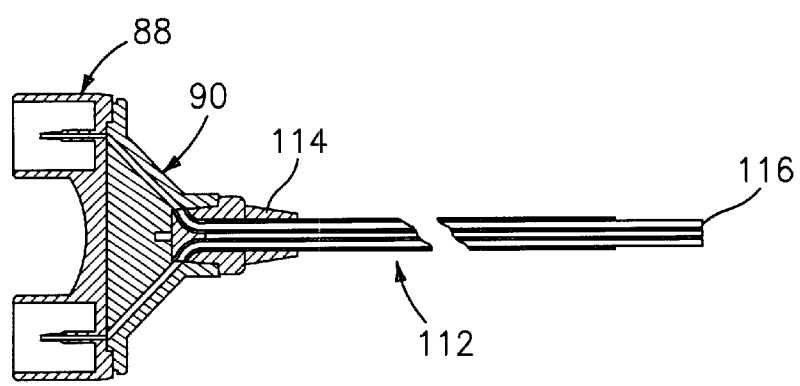
FIG. 17C is a cross-sectional view of the assembled components shown by FIG. 17B taken along line A—A in FIG. 17B.
Figure 18A:
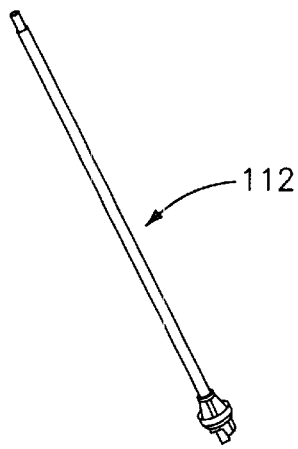
FIG. 18A is a perspective view of the laparoscopic tip shown by FIG. 17A.
Figure 18B:
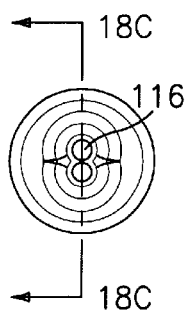
FIG. 18B is a top plan view of the laparoscopic tip shown by FIG. 18A.
Figure 18C:
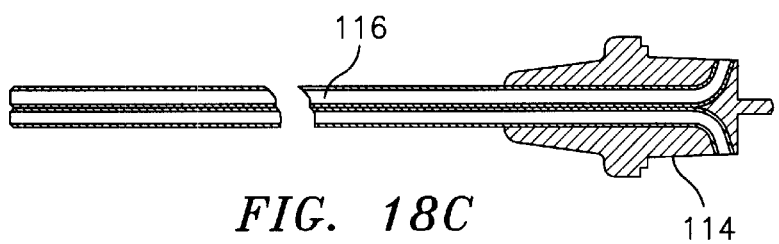
FIG. 18C is a cross-sectional view of the laparoscopic tip shown by FIG. 18A taken along line A—A in FIG. 18B.
Figure 19A:
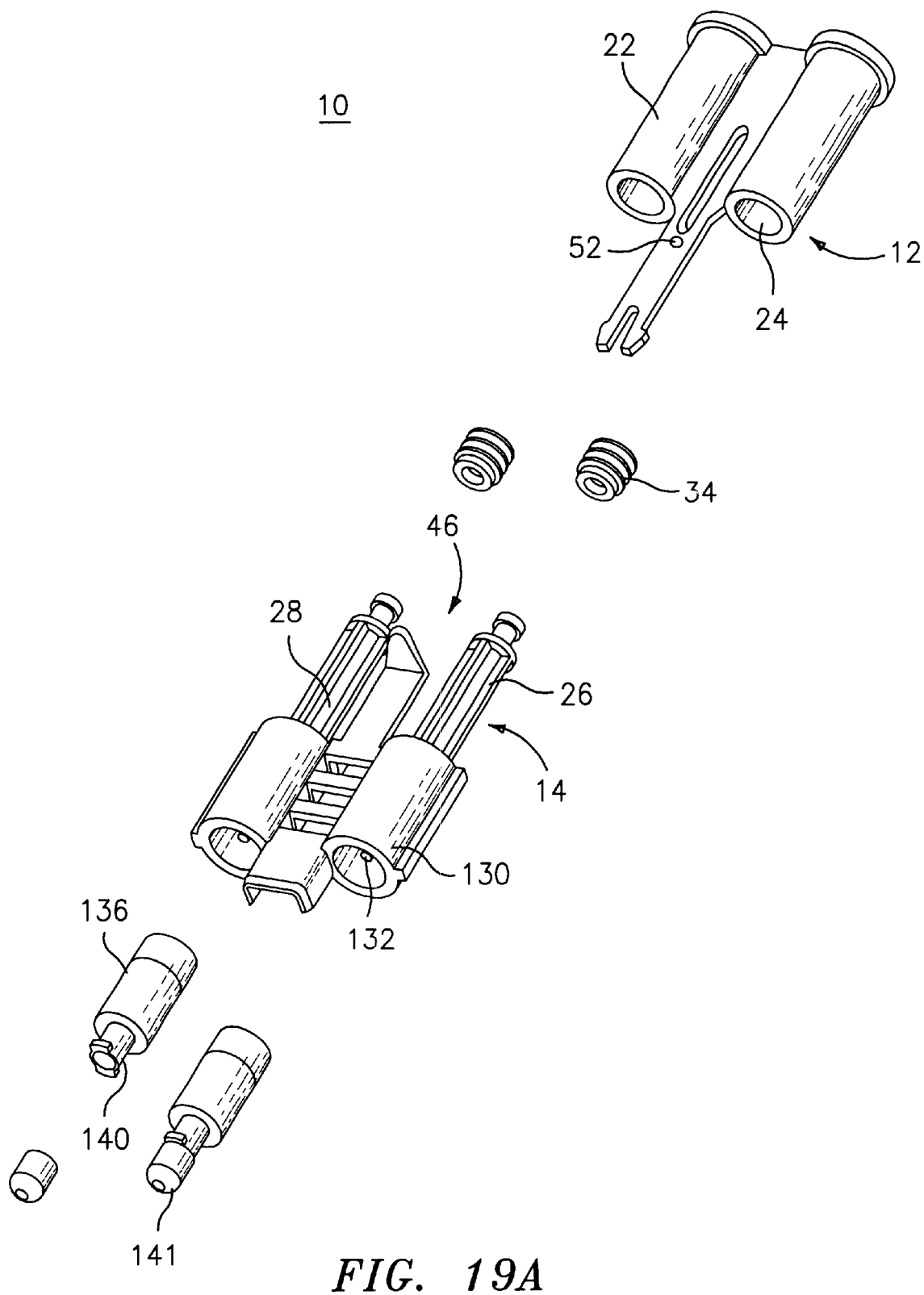
FIG. 19A is an exploded is an exploded view of two piston-type subassemblies.
Figure 20A:
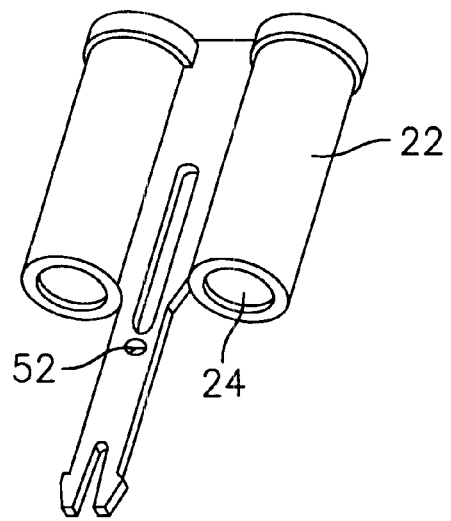
FIG. 20A is a perspective view of two cylindrical reservoirs of the subassemblies shown by FIGS. 19A–19E.
Figure 20B:
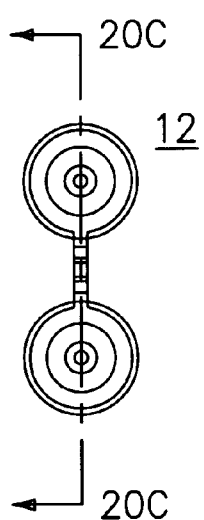
FIG. 20B is a bottom plan view of the two cylindrical reservoirs shown by FIG. 20A.
Figure 20C:
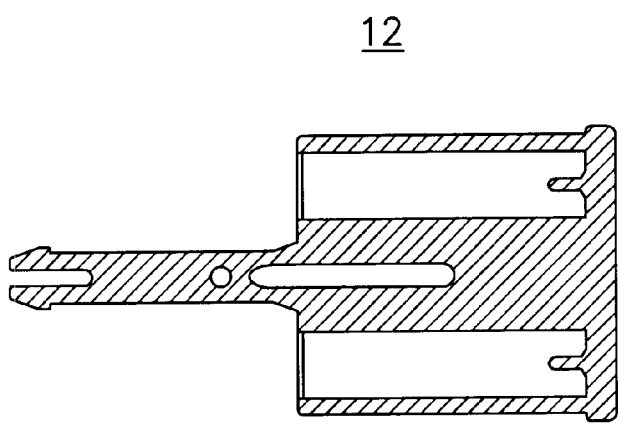
FIG. 20C is a cross-sectional view of the two cylindrical reservoirs taken along line A—A in FIG. 20B.
Figure 24A:
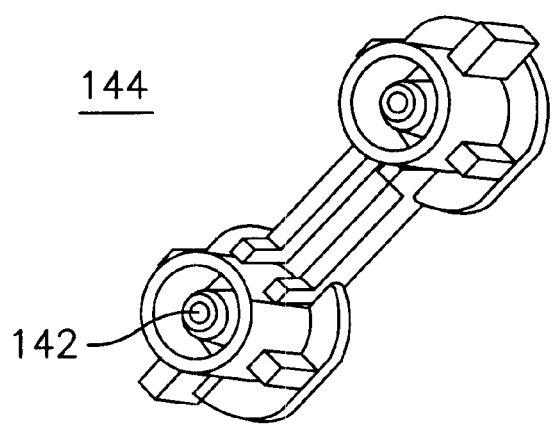
FIG. 24A is a perspective view of an adaptor for connecting check-valves to vials.
Figure 24B:
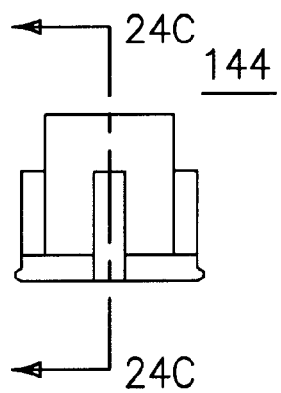
FIG. 24B is a side view of the adaptor shown by FIG. 24A.
Figure 24C:
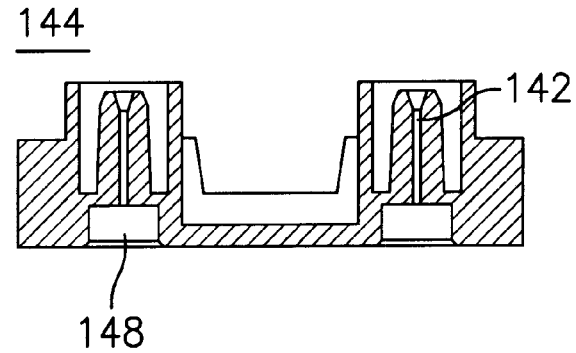
FIG. 24C is a cross-sectional view of the adaptor shown by FIG. 24A taken along line A—A in FIG. 24B.

Distal face 102 connects to proximal face 104 by snap-fitting distal face 102 into proximal face 104 of body tip 90 such that fluid communication is provided between hollow needles 98 and passageways 106 extending within body tip 90 (FIGS. 13A–13C). Passageways 106 lead to cavities 108 within collar 92 (FIGS. 14A–14C). Cavities 108 lead to openings 110 within nozzle body 94 (FIGS. 15A–15B) to dispense any solutions flowing through cavities 108 when seal 96 is absent. Specifically, the solutions are dispensed by moving reservoirs 22 distally to decrease the volumetric capacity therein and force the solutions distally towards openings 110.

With reference to FIGS. 17A–17C and 18A–18C, a laparoscopic tip 112 having an adaptor 114 for matingly engaging body tip 90 may be provided to the fibrin sealant applicator to provide fluid communication between passageways 106 and bores 116. It is contemplated that adaptor 88, body tip 90, and laparoscopic tip 112 are ultrasonically welded.

Reference will now be made to a second embodiment of the fibrin sealant applicator system in conjunction with FIGS. 19A–30D. The second embodiment works substantially the same as the first embodiment described above and identical reference numerals identify the same or similar components.

Figure 25A:
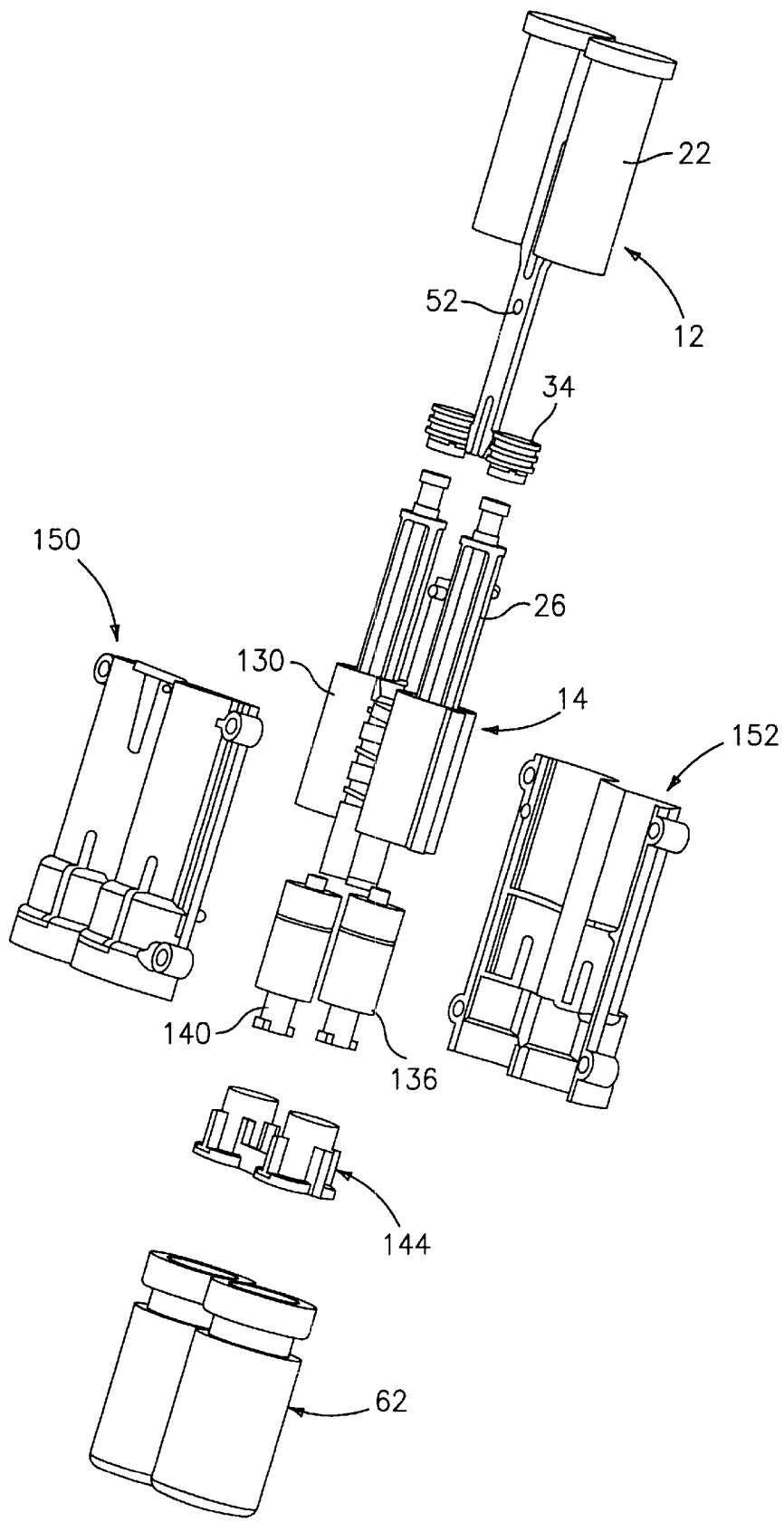
FIG. 25A is an assembly view showing coupling of the two piston-type sub-assemblies, the check-valves, the adaptor, and the vials.
Figure 25C:
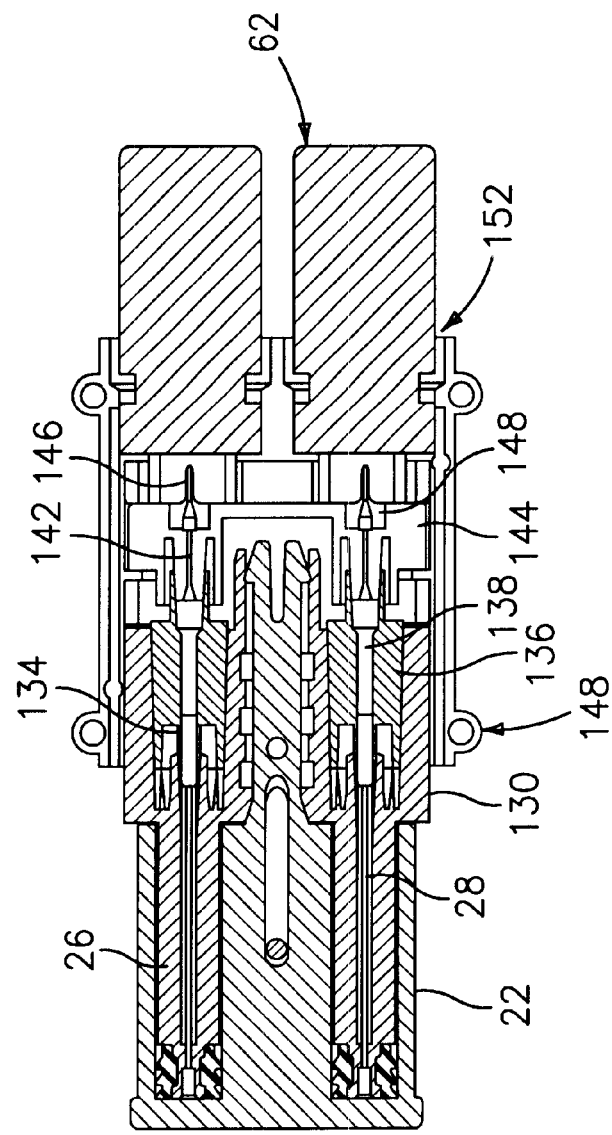
FIG. 25C is a cross-sectional view of the assembled components shown by FIG. 25B taken along line A—A in FIG. 25B.
Figure 25B:
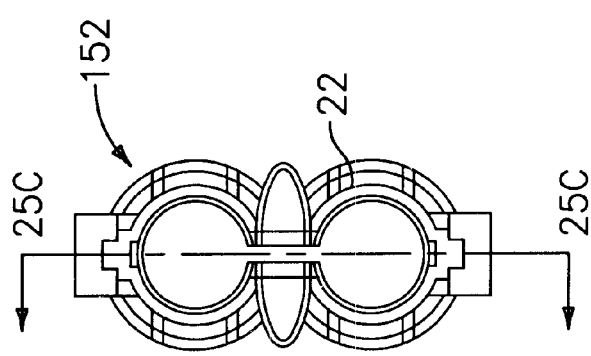
FIG. 25B is top plan view of the assembled components shown by FIG. 25A.

The second embodiment includes two piston-type sub-assemblies 10 each having a reservoir assembly 12 (FIGS. 20A–20C) and a piston assembly 14 (FIGS. 21A–21C). Piston assembly 14 includes two check-valve retainers 130 each having a compartment 132 therein. Each compartment 132 includes passageway 134 in fluid communication with bore 28. A check-valve 136 is placed within each check-valve retainer 130 having a bore 138 therethrough and a nozzle 140 covered by a seal 141 as shown by FIGS. 19A–19E. Each bore 138 is in fluid communication with a corresponding passageway 134 and each nozzle 140 is in fluid communication with a bore 142 within adaptor 144 (FIGS. 24A–24C) as shown by FIGS. 25A–25C. It is contemplated to provide each check-valve 136 with a valve for opening and closing bore 138 traversing therethrough to prevent and allow fluid communication between reservoir assembly 12 and the distal ends of check-valves 136.

With continued reference to FIGS. 25A–25C, each bore 142 is in fluid communication with a hollow distal needle 146 fitted within a recess 148 of adaptor 144. Hollow distal needles 146 provide fluid communication between reservoirs 22 and vials 62 when adaptor 144 is moved distally within coupling unit 148 and needles 146 contact and pierce a seal overlaying vials 62. Coupling unit 148 is similar in design and operation as coupling unit 56 with slight design modifications in top portion 150 (FIGS. 22A–22D) and bottom portion 152 (FIGS. 23A–23C) for housing check-valve retainers 130 and adaptor 144 therein.

Y-coupler dispensing unit assembly 86 (FIGS. 26A–26C) having adaptor 154 (FIGS. 27A–27C), body tip 90 (FIGS. 28A–28C), collar 92 (FIGS. 29A–29C) and nozzle body 94 (see FIGS. 15A–15B of the first embodiment) is fitted to check-valves 136 when vials 62, adaptor 144 and coupling unit 148 are removed from the two piston-type sub-assemblies 10 when the solutions have been formed and drawn into reservoirs 22 as shown by FIGS. 30A–30D.

Figure 27A:
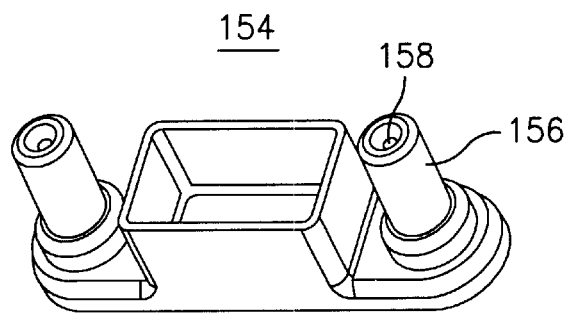
FIG. 27A is a perspective view of an adaptor of the Y-coupler shown by FIG. 26A.
Figure 27B:
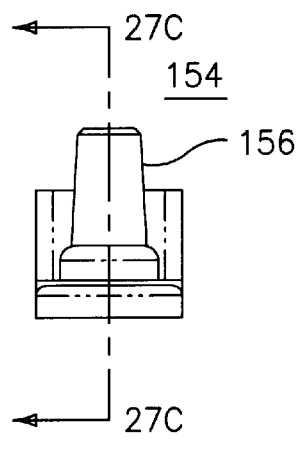
FIG. 27B is a side view of the adaptor shown by FIG. 27A.
Figure 27C:
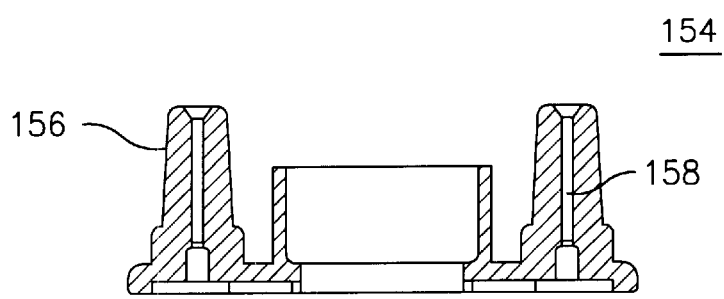
FIG. 27C is a cross-sectional view of the adaptor shown by FIG. 27A taken along line A—A in FIG. 27B.
Figure 28A:
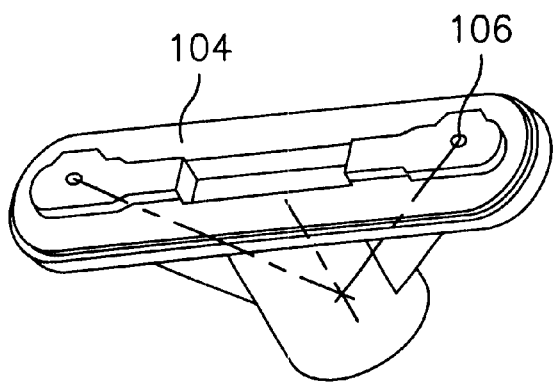
FIG. 28A is a perspective view of a body tip of the Y-coupler shown by FIG. 27A.
Figure 28B:
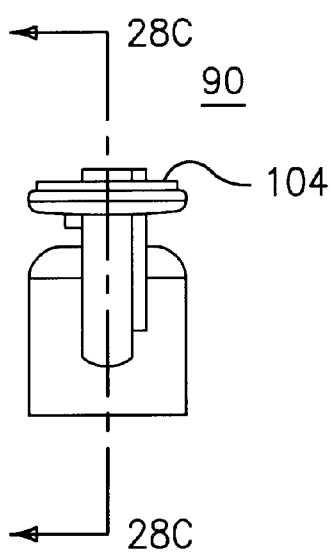
FIG. 28B is a side view of the body tip shown by FIG. 28A.
Figure 28C:
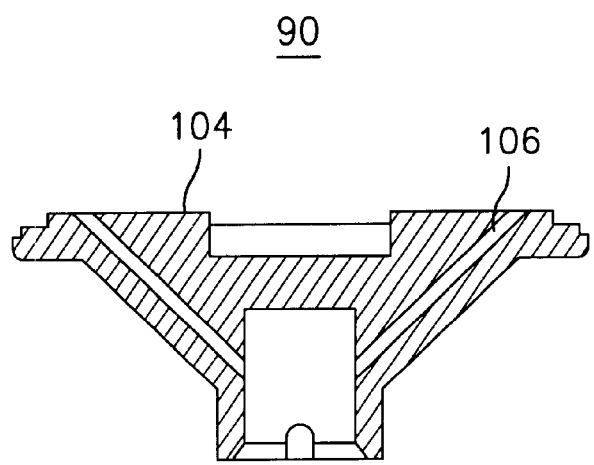
FIG. 28C is a cross-sectional view of the body tip shown by FIG. 28A taken along line A—A in FIG. 28B.
Figure 29A:
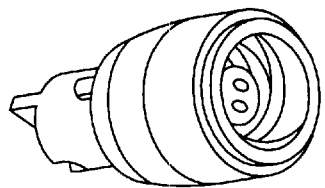
FIG. 29A is a perspective view of a collar of the Y-coupler shown by FIG. 27A.
Figure 29B:
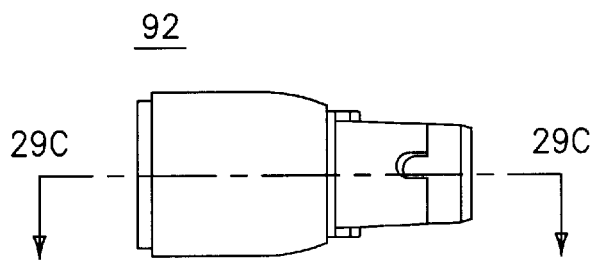
FIG. 29B is a side view of the collar shown by FIG. 29A.
Figure 29C:
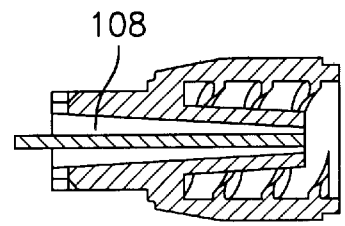
FIG. 29C is a cross-sectional view of the collar shown by FIG. 29A taken along line A—A in FIG. 29B.

Specifically, with reference to FIGS. 27A–27C, adaptor 154 of Y-coupler dispensing unit assembly 86 includes two male connectors 156 having a bore 158 therein for matingly engaging nozzles 140 of check-valves 136 for providing fluid communication between reservoirs 22 and openings 110 within nozzle body 94. With reference to FIGS. 30A–30D, the solutions can then be dispensed by distally moving reservoirs 22 to decrease the volumetric capacity therein as discussed above with respect to the first embodiment.

It is contemplated that a laparoscopic tip can also be provided for the second embodiment. It is further contemplated to coat the passageways and bores wherein the solutions flow with a non-stick polymer to prevent the solutions from attaching to the components of the fibrin sealant applicator and to allow the components to be readily cleaned. It is further contemplated that similar components of the two embodiments are manufactured from the same materials. Additionally, it is further contemplated to provide the components of the two embodiments as a kit. Therefore, it is understood that various modifications may be made to the embodiments disclosed herein.

Also, besides applying a fibrin sealant, the fibrin sealant applicator systems can be used to perform human or veterinary surgical procedures, such as applying antiseptics and medication. Therefore, the above description should not be construed as limiting, but merely as exemplifications of preferred embodiments. Those skilled in the art will envision other modifications within the scope and spirit of the above disclosure and appended claims.

What is claimed is:

1. An applicator system for dispensing a first solution and a second solution of a multicomponent biological adhesive, the applicator system comprising;

a piston-reservoir assembly having a reservoir sub-assembly coupled to a piston sub-assembly, said reservoir sub-assembly having two reservoirs and said piston sub-assembly having two pistons, each of said two reservoirs matingly engaging a corresponding one of said two pistons, said two pistons having fluid communication means for communicating fluid from said two reservoirs to a distal end of each of said two pistons; and a loading unit assembly configured for being coupled with said piston-reservoir assembly and at least two vials each storing at least one component of said multicomponent biological adhesive, said loading unit assembly having movable piercing means for moving towards said at least two vials and piercing a seal on each of said at least two vials, said loading unit assembly further having fluid communication means for communicating fluid from said distal end of each of said two pistons to an interior of each of said at least two vials by distally moving each of said two reservoirs toward each of said two pistons to decrease a volumetric capacity of each of said two reservoirs;

wherein each of said at least one component of said multicomponent biological adhesive is mixed with said fluid communicated from said distal end of each of said two pistons to said interior of each of said at least two vials to form said first and second solutions, said first and second solutions being communicated to a corresponding one of said two reservoirs via said fluid communication means of said loading unit assembly and said fluid communication means of said piston-reservoir assembly by proximally moving each of said two reservoirs away from each of said two pistons to increase said volumetric capacity of each of said two reservoirs, wherein said loading unit assembly being uncoupled from said piston-reservoir assembly for dispensing said first and second solutions of said multicomponent biological adhesive by compressing each of said two reservoirs toward each of said two pistons to decrease said volumetric capacity of each of said two reservoirs.

2. The applicator system according to claim 1, further comprising a dispensing unit assembly having at least two conduits and being configured for being coupled to said piston-reservoir assembly to align said at least two conduits with said fluid communication means of said two pistons.

3. The applicator system according to claim 2, wherein said dispensing unit assembly includes piercing means for piercing a seal fitted on each of said distal ends of said two pistons.

4. The applicator system according to claim 2, wherein said dispensing unit assembly is configured for performing laparoscopic surgical procedures.

5. The applicator system according to claim 3, wherein said piercing means includes two needles having a bore therethrough, said bore of each of said two needles being in fluid communication with said at least two conduits.

6. The applicator system according to claim 1, further comprising locking means for locking said reservoir sub-assembly to said piston sub-assembly to prevent distal movement of said two reservoirs towards said two pistons.

7. The applicator system according to claim 6, wherein said locking means includes a tab protruding from a rest bar of said piston sub-assembly, said tab being dimensioned to matingly engage a hole of said reservoir sub-assembly upon movement of said rest bar from a unlocked position to a locked position.

8. The applicator system of claim 1, further comprising a check-valve assembly having at least two check-valves configured for fitting at each of said distal ends of said two pistons, each of said at least two check-valves having a bore therethrough for providing fluid communication between said fluid communication means of said two pistons and said fluid communication means of said loading unit assembly.

9. The applicator system of claim 8, wherein each of said at least two check-valves includes a valve for preventing fluid communication between said fluid communication means of said two pistons and said fluid communication means of said loading unit assembly via each of said bores of said at least two check-valves.

10. The applicator system of claim 8, further comprising a dispensing unit assembly having at least two conduits and being configured for being coupled to said at least two check-valves to align said at least two conduits with a corresponding one of said two bores of said at least two check-valves.

11. The applicator system according to claim 1, wherein one of said at least two components is thrombin and another of said at least two components is fibrinogen.

12. The applicator system according to claim 11, wherein sterile water is communicated from said two reservoirs to said interior of each of said at least two vials to mix said sterile water with said thrombin and fibrinogen components to form said first and said second solutions, respectively, wherein said first solution is a thrombin solution and said second solution is a fibrinogen solution and said multicomponent biological adhesive is a fibrin sealant.

13. The applicator system according to claim 12, wherein said sterile water is hermetically sealed within said piston-reservoir assembly by providing distal and proximal seals to said distal ends of said two pistons and to proximal ends of said two pistons, respectively.

14. The applicator system according to claim 13, wherein said distal and proximal seals are manufactured from silicone.

15. The applicator system according to claim 1, wherein said piston-reservoir assembly is manufactured from polypropylene.

16. The applicator system according to claim 1, wherein said loading unit assembly is manufactured from ABS plastics.

17. A kit for dispensing a first solution and a second solution of a multicomponent biological adhesive, the kit comprising:
at least two piston assemblies each having a piston matingly engaging a reservoir storing a fluid therein, each of said pistons having fluid communication means for providing fluid communication between a corresponding one of said reservoirs and a distal end of said pistons for communicating said fluid stored within said reservoirs to said distal end of said pistons;
a loading unit assembly having a movable piercing shuttle, said movable piercing shuttle having a first end configured for coupling to said at least two piston assemblies and a second end configured for coupling to at least two vials each storing a component of said multicomponent biological adhesive, said loading unit assembly further having fluid communication means for communicating said fluid from said distal end of said pistons to an interior of each of said at least two vials by distally moving said reservoirs towards said pistons to mix said fluid with said components stored within said at least two vials to form said first and second solutions, said fluid communication means of said loading unit assembly further communicating said first and second solutions from said interior of each of said at least two vials to said reservoirs by proximally moving said reservoirs away from said pistons; and
a dispensing unit assembly having at least two conduits each configured to align with a corresponding one of said fluid communication means of each of said pistons when coupling said dispensing unit assembly to said distal ends of said at least two piston assemblies, wherein said first and second solutions are dispensed by said dispensing unit assembly by distally moving said reservoirs towards said pistons.

18. The kit according to claim 17, wherein said dispensing unit assembly includes piercing means for piercing a seal fitted on each of said distal ends of said two pistons.

19. The kit according to claim 17, wherein said dispensing unit assembly is configured for performing laparoscopic surgical procedures.

20. The kit according to claim 19, wherein said piercing means includes two needles having a bore therethrough, said bore of each of said two needles being in fluid communication with said at least two conduits.

21. The kit according to claim 17, further comprising a check-valve assembly having at least two check-valves configured for fitting at each of said distal ends of said two pistons.

22. The kit according to claim 21, wherein each of said at least two check-valves includes a bore therethrough for providing fluid communication between said fluid communication means of said two pistons and said fluid communication means of said loading unit assembly.

23. The kit according to claim 21, wherein each of said at least two check-valves includes a valve for preventing fluid communication through each of said bores.

24. The kit according to claim 21, wherein said dispensing unit assembly is configured for being coupled to said at least two check-valves to align said at least two conduits of said dispensing unit assembly with a corresponding one of said two bores of said at least two check-valves for providing fluid communication between said bores of said at least two check-valves and said at least two conduits of said dispensing unit assembly.

25. The kit according to claim 17, wherein said component stored by one of said at least two vials is thrombin and said component stored by another of said at least two vials is fibrinogen.

26. The kit according to claim 25, wherein said fluid stored within each of said reservoirs is sterile water capable of being communicated from said reservoirs to said interior of each of said at least two vials to mix said sterile water with said thrombin and fibrinogen to form said first and said second solutions, respectively, wherein said multicomponent biological adhesive is a fibrin sealant.

27. The kit according to claim 26, wherein said sterile water is hermetically sealed within said at least two piston assemblies by providing distal and proximal seals to said distal ends of said two pistons and to proximal ends of said two pistons, respectively.

28. The kit according to claim 27, wherein said distal and proximal seals are manufactured from silicone.

29. The kit according to claim 17 wherein said at least two piston assemblies are manufactured from polypropylene.

30. The kit according to claim 17, wherein said loading unit assembly is manufactured from ABS plastics.

31. The kit according to claim 17, wherein said dispensing unit assembly includes a plurality of ultrasonically welded components.

* * * * *